US007686813B2

(12) United States Patent
Stutz et al.

(10) Patent No.: US 7,686,813 B2
(45) Date of Patent: Mar. 30, 2010

(54) TRACTION APPARATUS

(75) Inventors: Heinrich Stutz, Frauenfeld (CH);
Simon-Paul Dominati, Marseilles (FR);
Bernhard Gyssler, Thalwil (CH); Hervé Houdemer, Winterthur (CH); José Romero, Kuesnacht (CH); Claudio Castelli, Bergamo (IT)

(73) Assignee: Zimmer, GmbH, Winterthur (CH)

( * ) Notice: Subject to any disclaimer, the term of this patent is extended or adjusted under 35 U.S.C. 154(b) by 1067 days.

(21) Appl. No.: 10/839,984

(22) Filed: May 5, 2004

(65) Prior Publication Data
US 2005/0027226 A1 Feb. 3, 2005

(30) Foreign Application Priority Data
May 6, 2003 (EP) ................... 03010177
Dec. 22, 2003 (DE) ................ 103 60 433

(51) Int. Cl.
*A61B 17/60* (2006.01)
(52) U.S. Cl. ........................................................ 606/90
(58) Field of Classification Search ................... 606/90
See application file for complete search history.

(56) References Cited

U.S. PATENT DOCUMENTS

| 4,349,018 A | 9/1982 | Chambers |
| 4,364,389 A | 12/1982 | Keller |
| 4,501,266 A | 2/1985 | McDaniel |
| 4,524,766 A | 6/1985 | Petersen |
| 4,566,448 A | 1/1986 | Rohr, Jr. |
| 4,574,794 A | 3/1986 | Cooke et al. |
| 4,646,729 A | 3/1987 | Kenna et al. |
| 4,738,253 A | 4/1988 | Buechel et al. |
| 4,759,350 A | 7/1988 | Dunn et al. |
| 4,825,857 A | 5/1989 | Kenna |
| 4,938,762 A | 7/1990 | Wehrli |
| 5,116,338 A * | 5/1992 | Poggie et al. ............... 606/90 |
| 5,122,144 A | 6/1992 | Bert et al. |
| 5,213,112 A * | 5/1993 | Niwa et al. ............... 600/587 |
| 5,234,433 A | 8/1993 | Bert et al. |
| 5,326,363 A | 7/1994 | Aikins |
| 5,342,367 A | 8/1994 | Ferrante et al. |
| 5,364,402 A | 11/1994 | Mumme et al. |
| 5,468,244 A | 11/1995 | Attfield et al. |
| 5,540,696 A | 7/1996 | Booth, Jr. et al. |
| 5,549,686 A | 8/1996 | Johnson et al. |
| 5,562,675 A | 10/1996 | McNulty et al. |
| 5,597,379 A | 1/1997 | Haines et al. |

(Continued)

FOREIGN PATENT DOCUMENTS

DE  203 03 498  8/2003

(Continued)

*Primary Examiner*—Thomas C Barrett
*Assistant Examiner*—Nicholas Woodall
(74) *Attorney, Agent, or Firm*—Baker & Daniels LLP

(57) ABSTRACT

The invention relates to a hydraulic traction apparatus for surgery, in particular for knee surgery, having at least one pair of working sections which can be adjusted relative to one another and at least one exchangeable piston in cylinder arrangement made of plastic whose piston is releasably coupled to the one working section and whose cylinder is releasably connected to the other working section and which is stiffened by an outer support mount supporting the cylinder from the outside and by at least one inner reinforcement insert which can be inserted into the cylinder together with the piston.

23 Claims, 18 Drawing Sheets

U.S. PATENT DOCUMENTS

Figure 2:
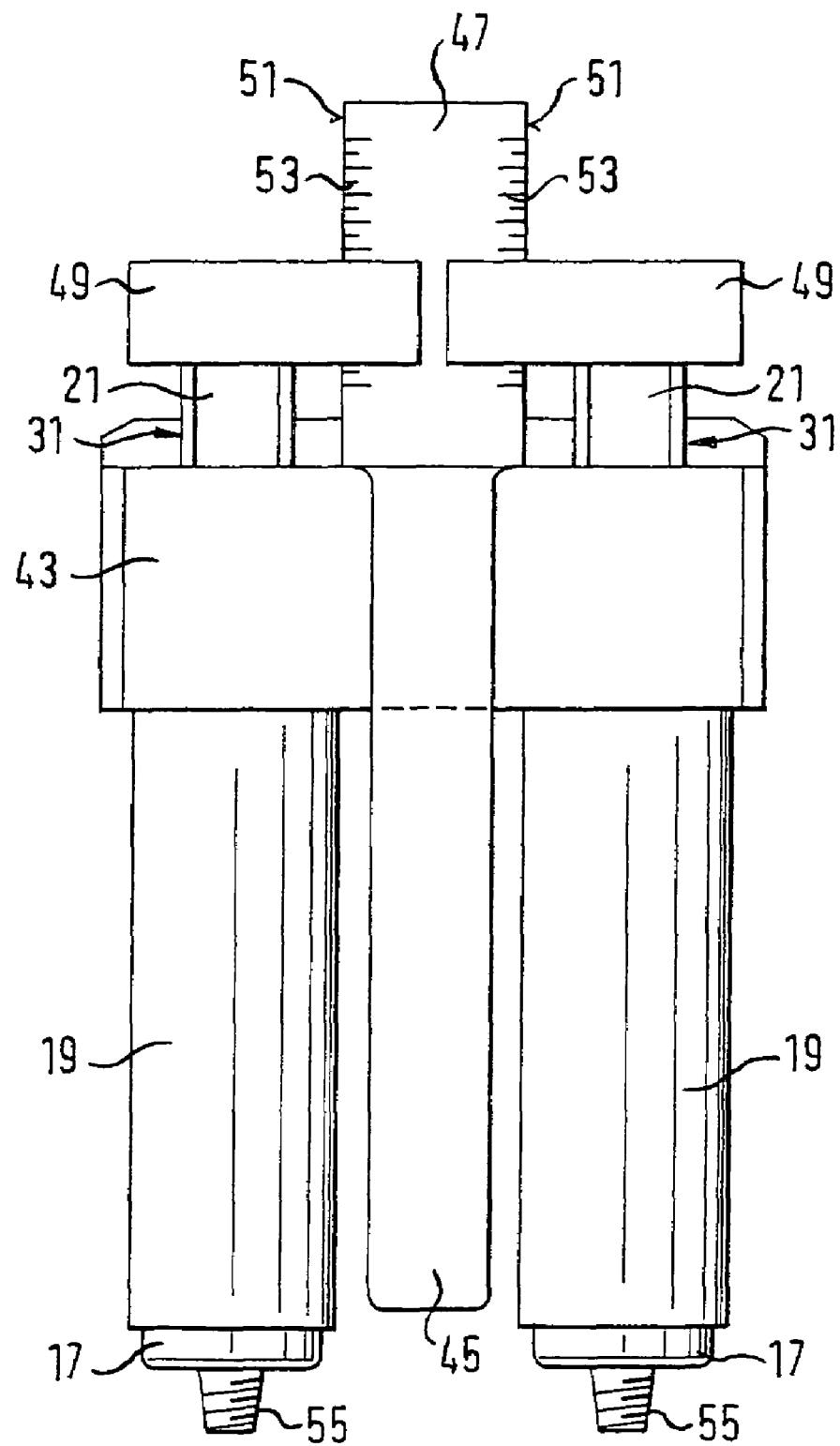

| | | | |
|---|---|---|---|
| 5,643,272 A | 7/1997 | Haines et al. | |
| 5,669,914 A | 9/1997 | Eckhoff | |
| 5,681,320 A | 10/1997 | McGuire | |
| 5,688,280 A | 11/1997 | Booth, Jr. et al. | |
| 5,733,292 A | 3/1998 | Gustilo et al. | |
| 5,800,438 A | 9/1998 | Tuke et al. | |
| 5,911,723 A | 6/1999 | Ashby et al. | |
| 6,022,377 A | 2/2000 | Nuelle et al. | |
| 6,056,756 A | 5/2000 | Eng et al. | |
| 6,168,601 B1 | 1/2001 | Martini | |
| 6,296,646 B1 | 10/2001 | Williamson | |
| 6,478,799 B1 | 11/2002 | Williamson | |
| 6,482,209 B1 | 11/2002 | Engh et al. | |
| 6,575,980 B1 | 6/2003 | Robie et al. | |
| 6,648,896 B2 * | 11/2003 | Overes et al. | 606/90 |
| 6,695,848 B2 | 2/2004 | Haines | |
| 6,758,850 B2 | 7/2004 | Smith et al. | |
| 7,094,241 B2 | 8/2006 | Hodorek et al. | |
| 7,201,755 B2 | 4/2007 | Faoro et al. | |
| 2003/0100906 A1 | 5/2003 | Rosa et al. | |
| 2003/0187452 A1 | 10/2003 | Smith et al. | |
| 2004/0097951 A1 | 5/2004 | Steffensmeier | |
| 2004/0249387 A1 | 12/2004 | Faoro | |
| 2005/0143746 A1 | 6/2005 | Steffensmeier et al. | |
| 2005/0182415 A1 | 8/2005 | Steffensmeier et al. | |
| 2006/0149276 A1 | 7/2006 | Grimm | |

FOREIGN PATENT DOCUMENTS

| | | |
|---|---|---|
| DE | 10335410 A1 | 2/2005 |
| EP | 0327249 B1 | 8/1989 |
| EP | 0 709 061 | 5/1996 |
| EP | 0809969 A2 | 5/1997 |
| EP | 1226788 A1 | 1/2002 |
| EP | 0 809 969 | 10/2002 |
| EP | 1245193 A1 | 10/2002 |
| EP | 1348382 A2 | 10/2003 |
| FR | 2 619 168 | 2/1989 |
| FR | 2 648 699 | 12/1990 |
| FR | 2 679 766 | 2/1993 |
| SU | 1237187 A1 | 6/1986 |
| SU | 1745227 A1 | 7/1992 |
| WO | 01/66021 | 9/2001 |
| WO | 01/85038 | 11/2001 |
| WO | WO 01/85038 A1 | 11/2001 |

* cited by examiner

FIG. 1
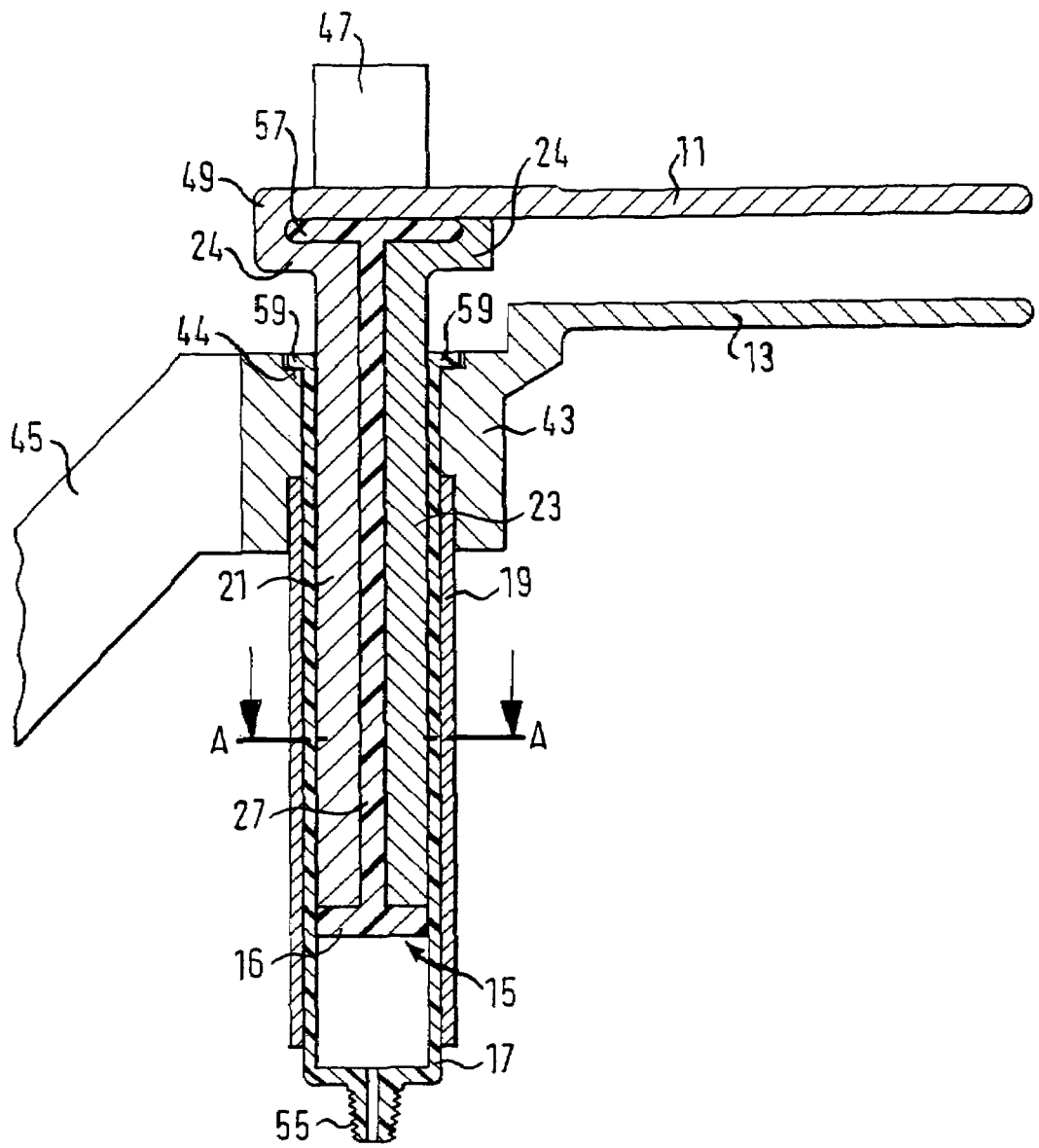
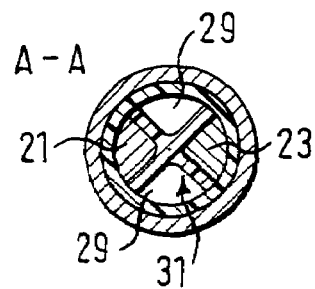

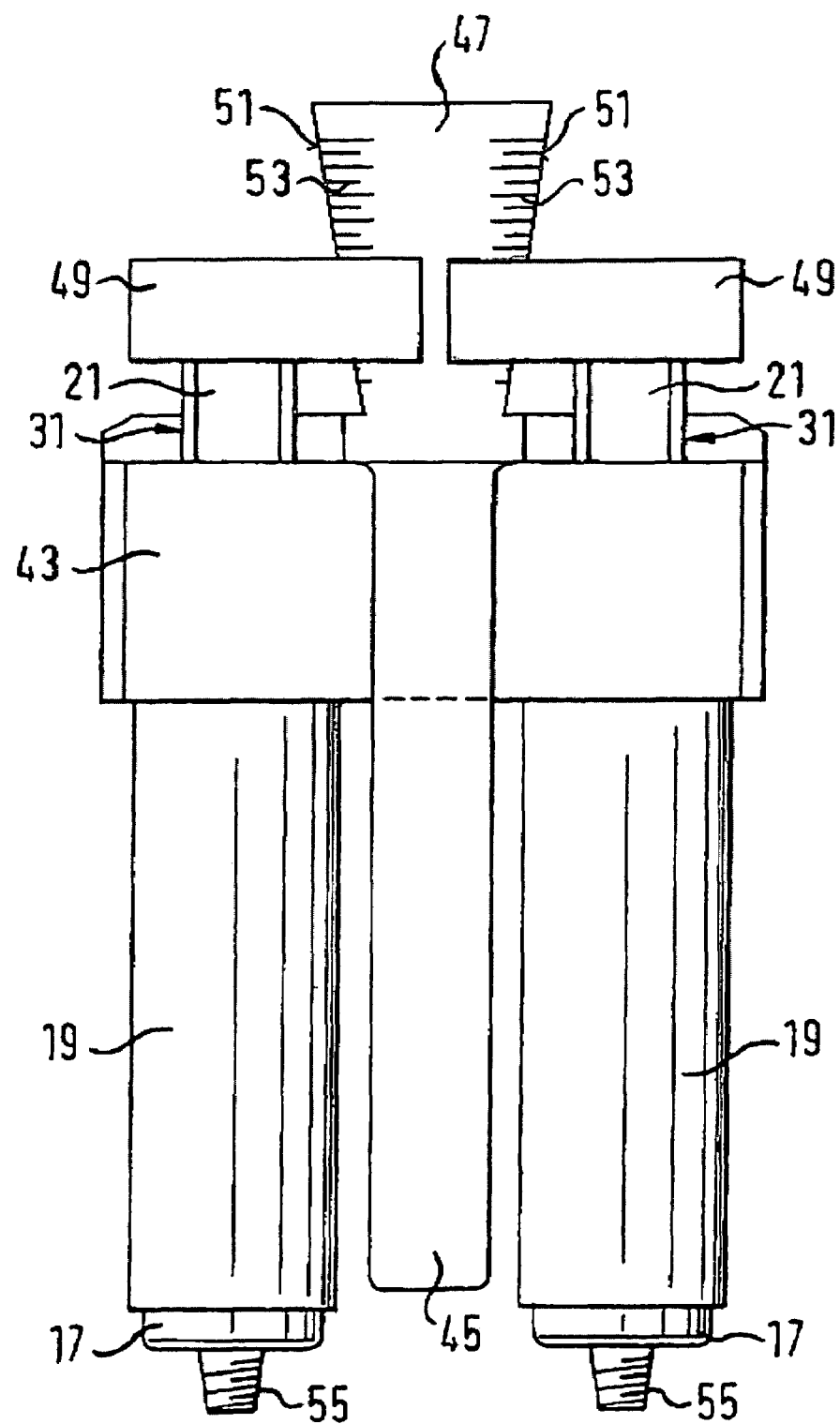

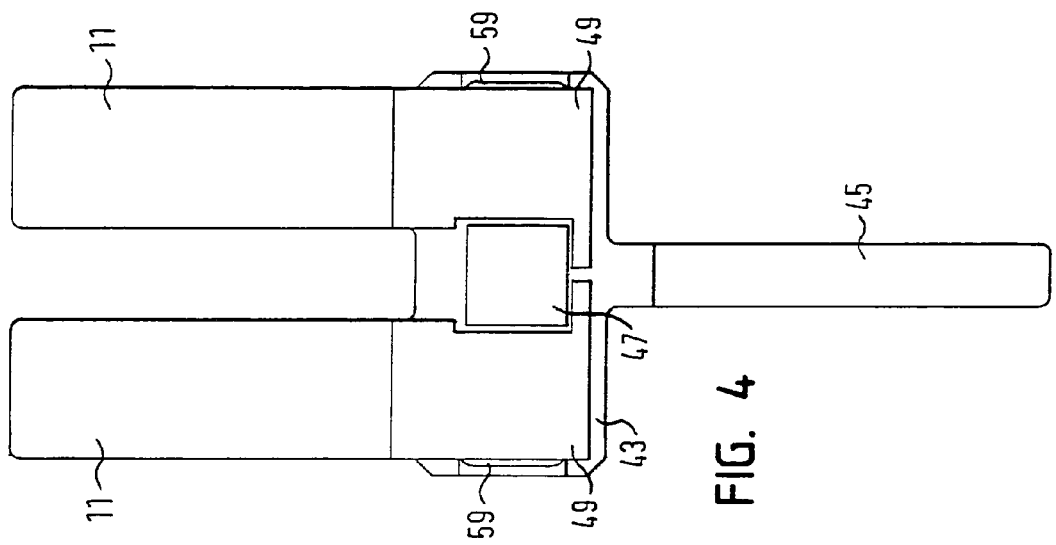
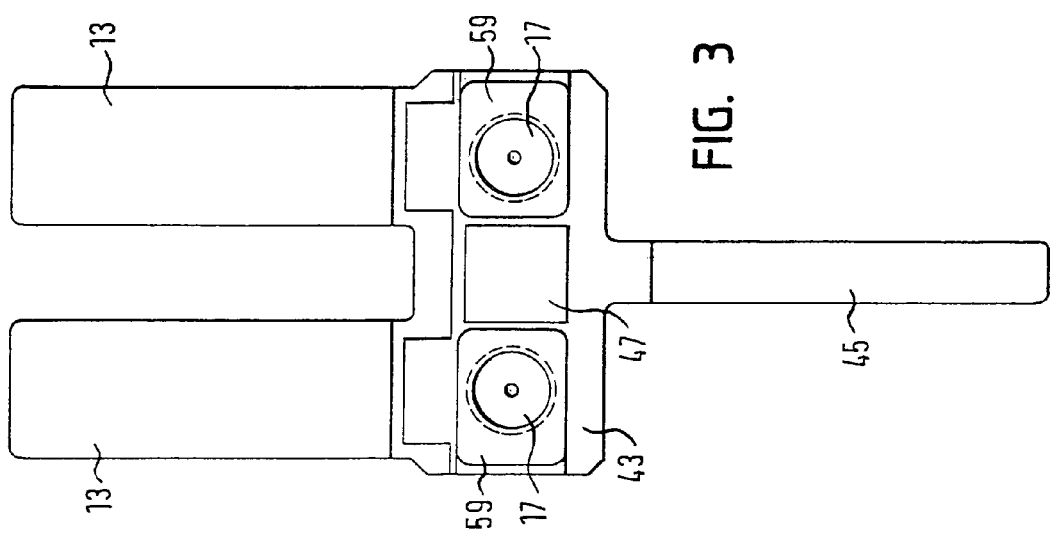

$F_1 < F_2$

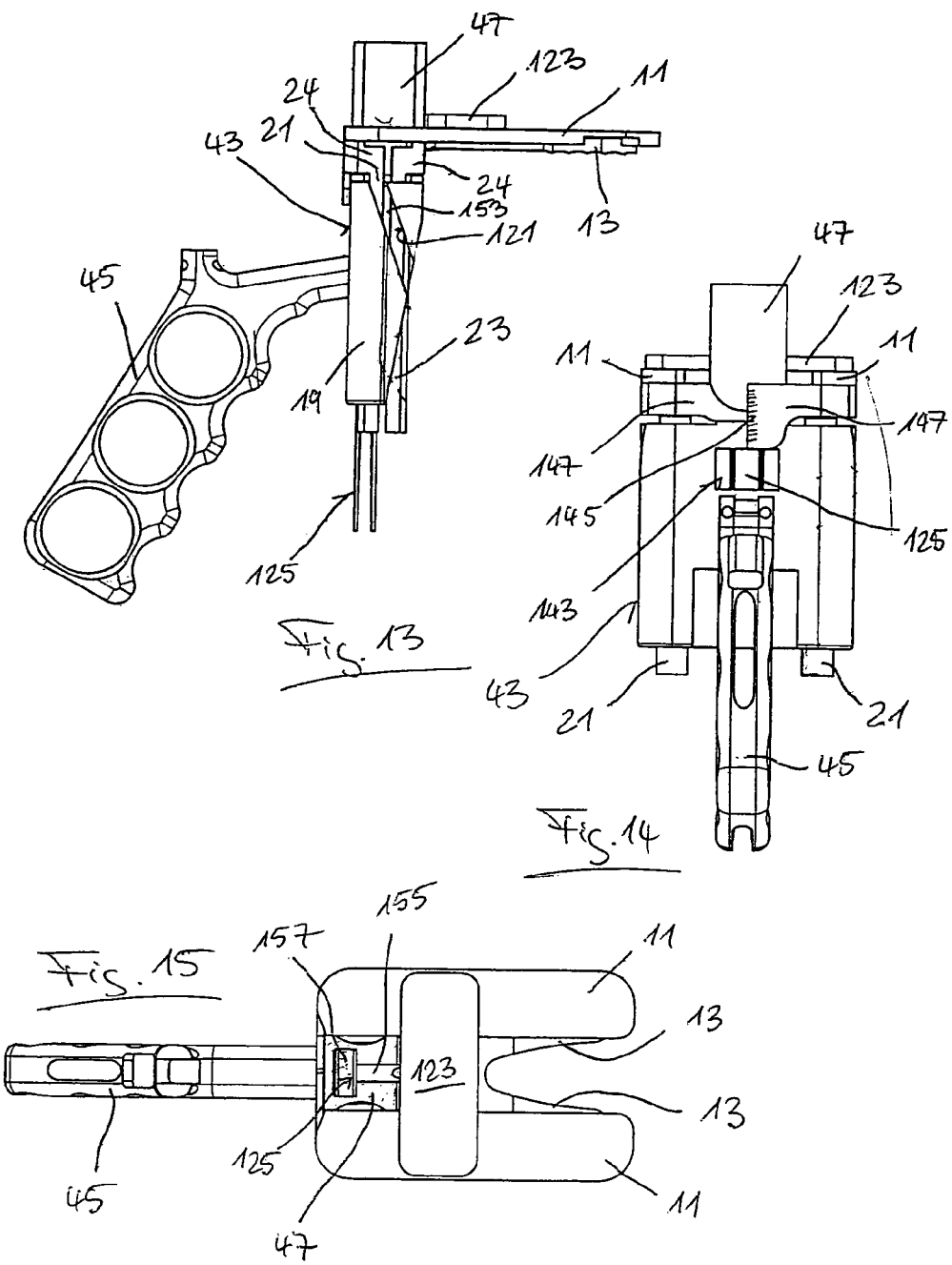

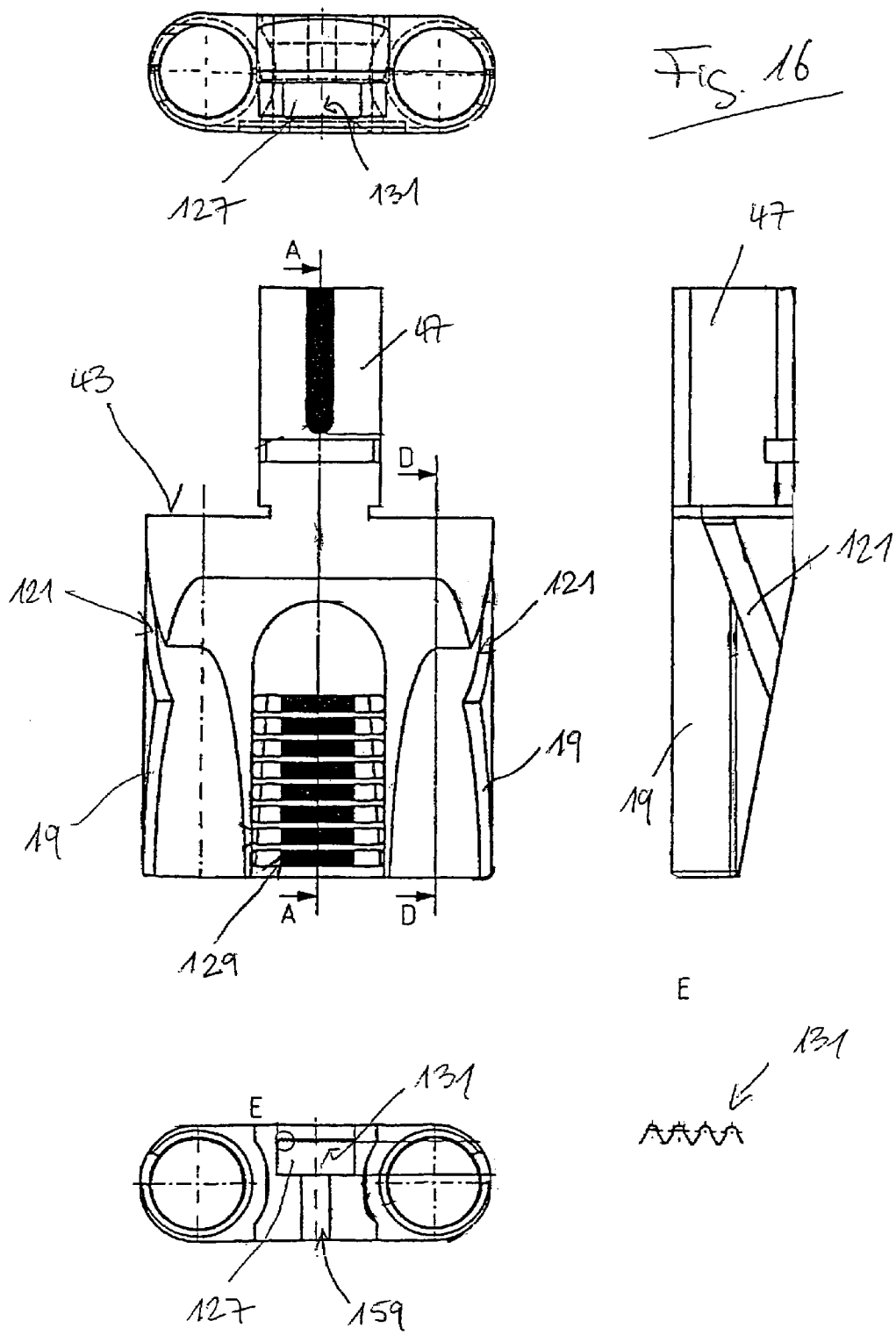

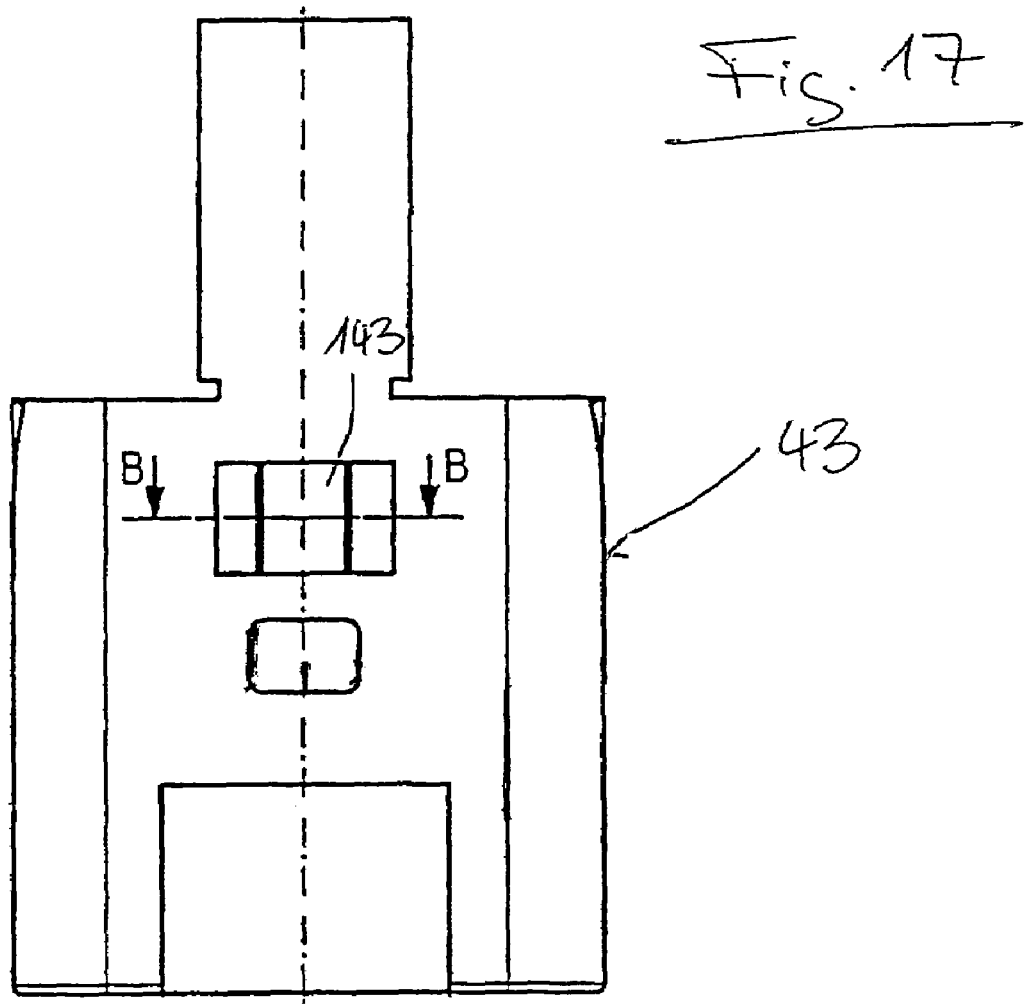
Fig. 17
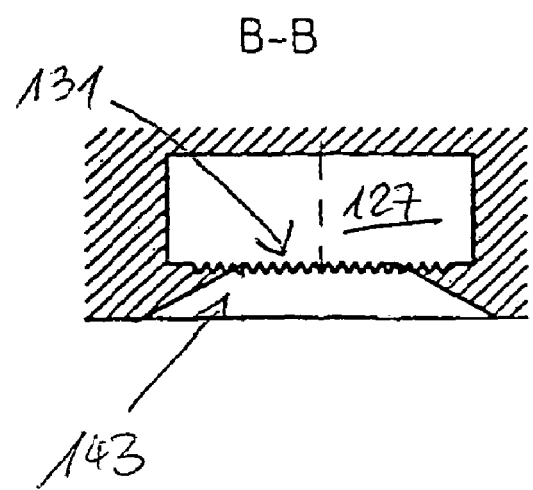
B-B

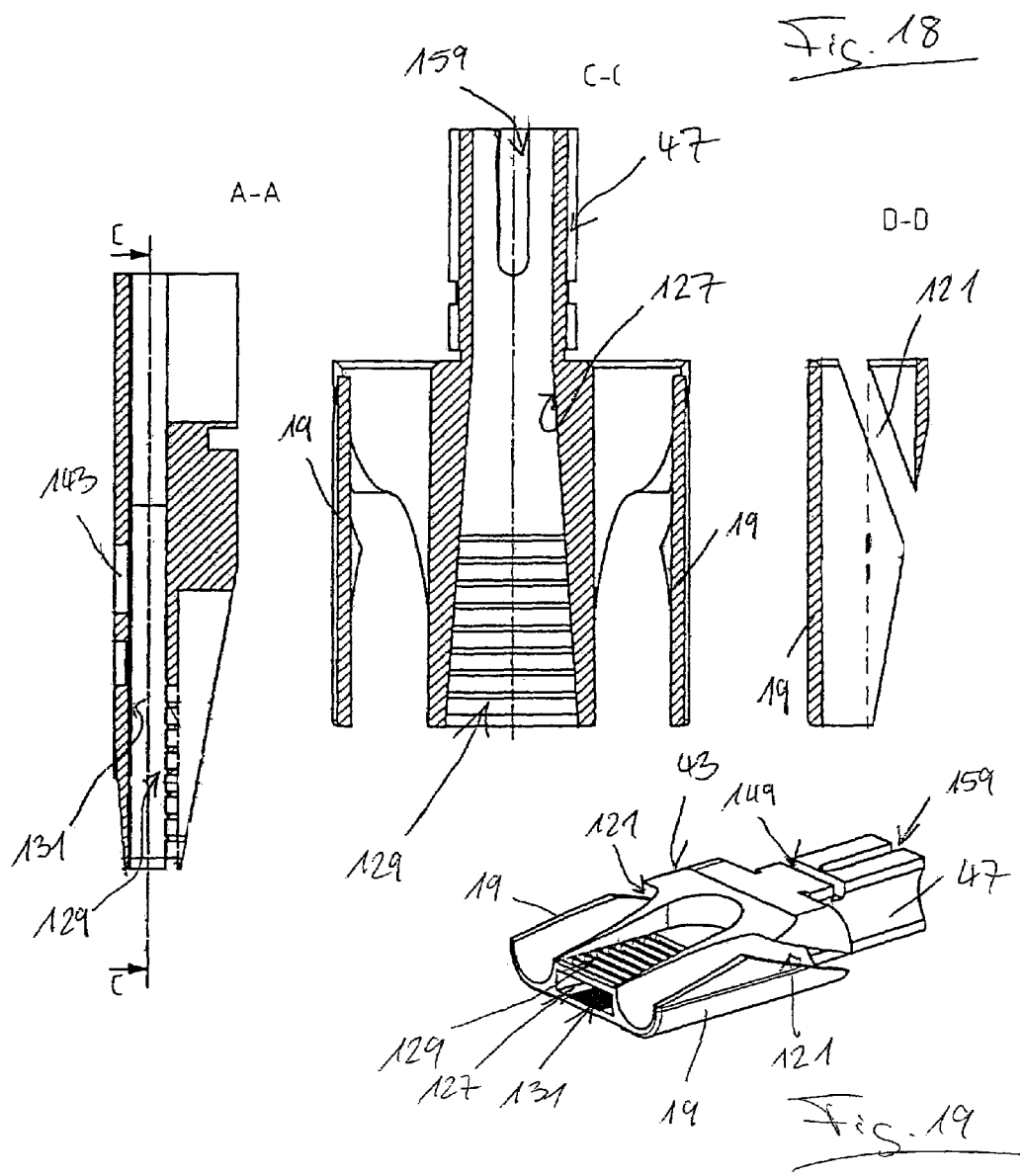

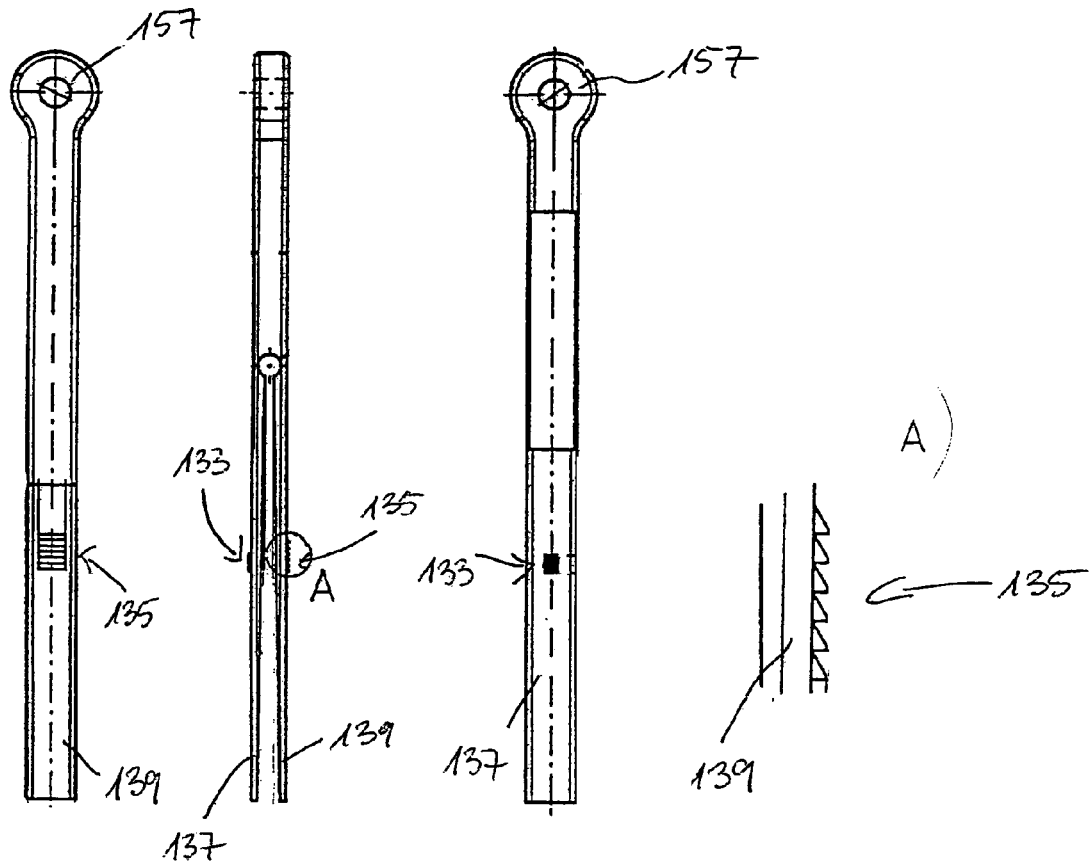
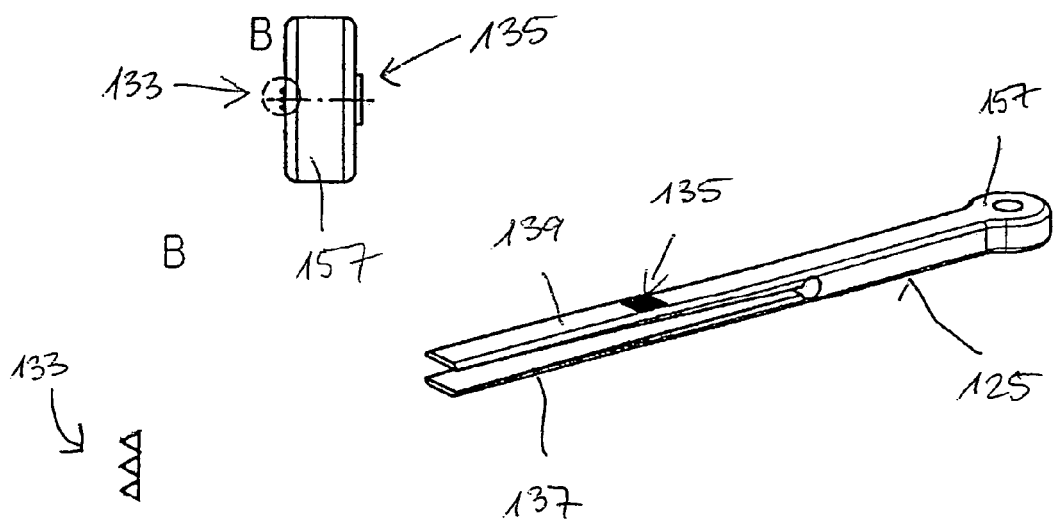
Fig. 22

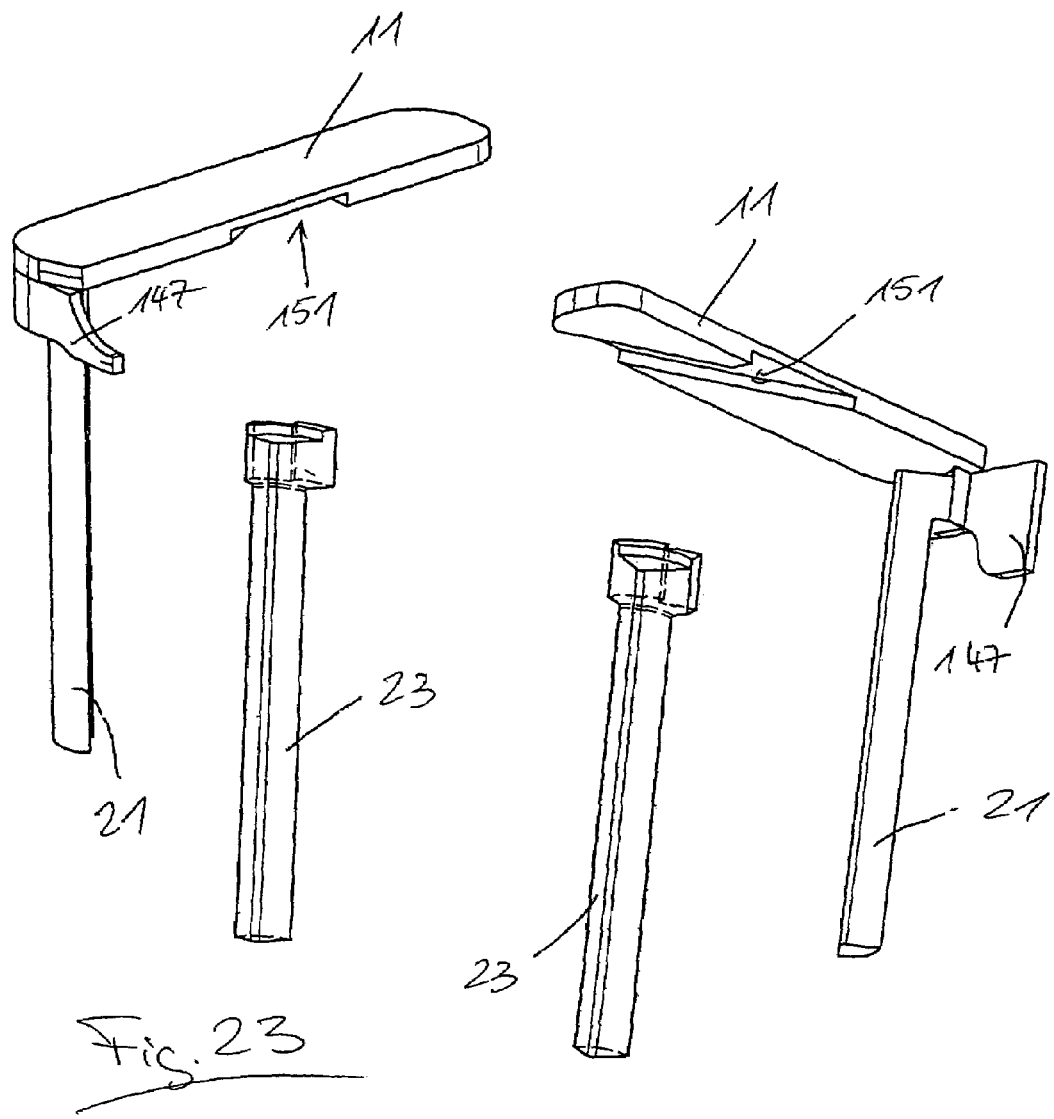

TRACTION APPARATUS

The invention relates to a hydraulic traction apparatus for surgery, in particular for knee surgery.

Traction devices which can be used in the context of knee surgery are generally known and serve to spread the knee, i.e. to enlarge the spacing between the femur and the tibia. The purpose of this is to bring the femur and the tibia into their natural relative positions during the knee surgery. The surgeon attempts to determine this natural relative position with reference to the natural tension of the ligaments. The surgeon has no additional aids available for this, i.e. the surgeon fixes the relative position between the femur and the tibia, which forms the basis for the further operation, only "by touch".

The surgeon also has to rely on his "touch" in other surgery to be carried out on the knee due to a lack of additional aids being available. In the case of implants of anterior cruciate ligaments, for example, it is thus a question of giving the ligament a ligament tension on insertion which corresponds to the natural motion of the knee joint.

It is the object of the invention to provide a traction apparatus for surgery which provides the opportunity, with a simple design and simple handling, to made additional information available to the surgeon during the operation.

This object is satisfied by the features of claim 1 and in particular in that the traction apparatus includes at least one pair of working sections which are adjustable relative to one another and at least one exchangeable piston in cylinder arrangement made of plastic whose piston is releasably coupled to the one working section and whose cylinder is releasably coupled to the other working section and which is stiffened by an outer support mount which supports the cylinder from the outside as well as by at least one inner reinforcement insert which can be inserted into the cylinder together with the piston.

The invention provides a hydraulic traction apparatus which is characterized in that the piston in cylinder arrangement is exchangeable and is made of plastic. This advantageously allows the use of favorably priced disposable parts for the piston in cylinder arrangement which consequently do not have to be sterilized repeatedly.

The support mount provided in accordance with the invention and the reinforcement insert insertable into the cylinder together with the piston increase the bending strength of the piston in cylinder arrangement. The traction apparatus is hereby in a position overall to absorb comparatively large forces due to the stiffening in accordance with the invention despite the manufacture of the actual piston in cylinder arrangement in plastic so that external forces acting on the working sections connected to the piston and to the cylinder can be absorbed by the support mount and by the reinforcement insert. Non-acceptable deformations of the piston in cylinder arrangement are hereby reliably avoided so that defined geometrical relationships prevail at every point in time of the operation and a parallelism of tongue-shaped platforms formed by the working sections which is in particular provided is always present.

Preferred embodiments of the invention are recited in the dependent claims, in the description and in the drawing.

The piston and the cylinder can thus each be disposable parts manufactured by the injection molding process. If the piston in cylinder arrangement should include further components, all these components are preferably provided for disposable use, whereby a cost favorable manufacture and—due to the omission of the necessity of repeated sterilization—simple handing are ideally combined.

The support mount and the reinforcement insert are preferably manufactured from a material with a higher bending strength than the plastic of the piston in cylinder arrangement. In particular metal or fiber reinforced plastic is used for this purpose.

The piston and the reinforcement insert can form a compact piston unit in the assembled state which completely fills the interior of the cylinder at least over a partial peripheral region.

In a particularly preferred embodiment, the piston in cylinder arrangement is formed by a commercial disposable syringe. A mass-produced article which can be manufactured in an extremely cost favorable manner hereby becomes a central component of a hydraulic traction apparatus for knee operations in a particularly elegant manner.

Provision can furthermore be made in accordance with the invention for a free space present between the inner wall of the cylinder and a piston rod to be at least partly filled by the reinforcement insert. Free spaces which are anyway present, such as commercial syringes have, can hereby be utilized for a stiffening reinforcement or rear filling by means of the at least one reinforcement insert.

Furthermore, at least one chamber which is present in the cylinder, is bounded by a rib structure of a piston rod which extends up to the inner wall of the cylinder and is in particular cross-shaped or X-shaped in cross-section, can be at least partly filled by the reinforcement insert.

At least one pair of chambers disposed opposite one another can be at least partly filled by a reinforcement insert.

Provision is furthermore made in accordance with the invention for the reinforcement insert to completely fill the interior of a tubular piston rod, which is guided at the inner wall of the cylinder, at least over a partial peripheral region.

It is not necessarily required in accordance with the invention to reinforce the piston such that the cylinder is completely filled over its whole cross-sectional area. It is preferred for the inner reinforcement to extend over the whole available length of the piston in cylinder arrangement. The stability and bending strength of the piston in cylinder arrangement is hereby ensured for every piston position and in particular also with a piston moved comparatively far out.

The piston in cylinder arrangement can be made such that it can be coupled to the working sections in the assembled state. The handling capability of the traction apparatus in accordance with the invention is hereby substantially facilitated.

At least one reinforcement insert can be fixedly connected to the working section. This makes a particularly stable design of high stiffness possible. Furthermore, at least one reinforcement insert can be provided in the form of a separate component.

The support mount for the cylinder and the working section which can be coupled to the cylinder can be fixedly connected to a carrier member. The number of individual components of the traction apparatus in accordance with the invention is hereby kept particularly low, which advantageously facilitates the handling and in particular the sterilization of the apparatus.

A handle, which is preferably fixedly connected to the carrier member, can be provided at the opposite side of the piston in cylinder arrangement from the working sections.

It is furthermore proposed in accordance with the invention that the working section which can be coupled to the cylinder is fixedly connected to a functional block which extends parallel to the traction direction and which is formed as a security against relative rotation and/or deflection for the working section which can be coupled to the piston.

A correct relative position between the two working sections can also be ensured with relatively large external forces acting on the working sections for all piston positions by such a functional block.

The functional block can have an outer cross-section deviating from a circular shape and can have a guide section of the working section engaged around it in a manner securing against relative rotation at least over a partial peripheral region.

Provision can furthermore be made for the functional block to have an abutment surface which is slightly inclined with respect to the traction direction, runs toward the longitudinal axis of the piston in cylinder arrangement in the direction of increasing traction length and cooperates with the working section in a manner securing against deflection.

The functional block is preferably provided with a display device at which a measure for the traction length can be read off. The display device can be provided in the form of a scale attached to an outer side of the functional block. Knee surgery can be made reproducible simply and in a reliable manner in that a measure for the traction length and thus for the spacing between the stretched working sections is made available in this manner.

The piston in cylinder arrangement can furthermore be provided with a display device, in particular in the form of a scale attached to the cylinder. In the case of use of a disposable syringe as the piston in cylinder arrangement, the scale anyway provided at the cylinder of the syringe can be utilized.

It is furthermore proposed in accordance with the invention for a fluid supply device for the piston in cylinder arrangement to include a syringe operable by hand, in particular a disposable syringe.

At least one pressure display device can be connected to a fluid line connecting the piston in cylinder arrangement with a fluid supply device. A measure for the traction force acting between the work sections is hereby made available. If ligaments are tightened in the operation, a measure for the respective ligament tension can consequently be read off at the pressure display device. This in turn makes it possible to make the surgery reproducible.

In a further preferred embodiment of the invention, the piston in cylinder arrangement is a component of a closed hydraulic system which can be handled as a unit and which additionally includes at least one fluid supply device, a fluid line connecting the piston in cylinder arrangement to the fluid supply device and a hydraulic fluid, in particular water, and can be coupled as a whole to the working sections. Such a closed hydraulic system can in particular be sterilized as a whole and can be coupled to the remaining components or assemblies of the traction apparatus, which substantially facilitates the use. In the preparation or during the operation, the previously sterilized hydraulic system only has to be removed from the packaging and to be coupled to the working sections. Complicated and time-consuming connection or venting work is not required.

In accordance with a further embodiment of the invention, at least two piston in cylinder arrangements are provided which act in parallel directions in the state coupled to the working sections.

An apparatus with two piston in cylinder arrangements disposed next to one another and each with associated working sections can in particular be used for bicompartmental operations for the insertion of bicondylar knee prostheses.

The piston in cylinder arrangements are preferably controllable independently of one another, i.e. can be acted on by hydraulic fluid such that the spacing between the femur and the tibia can be set at different sizes in the two compartments.

The piston in cylinder arrangements are preferably connected to a common fluid supply device during use.

Furthermore, the piston in cylinder arrangements can in each case alternatively be connectable to the fluid supply or separable from the fluid supply independently of one another by on/off valves arranged in a fluid line connecting the piston in fluid arrangements to a fluid supply device.

For the setting of desired spacings between the femur and the tibia, the working sections are preferably made such that they form a spread section which can be introduced between the femur and the tibia and which extend substantially perpendicular to the traction direction. The working sections can each be provided in the form of a plate-shaped tongue.

The traction apparatus in accordance with the invention is not exclusively usable for the pressing apart of the tibia and the femur, but can also be used in the context of other surgery, in particular in the region of the knee, in which parts should be moved relative to one another and it is desirable to obtain additional information during the course of the surgery, in particular on the instantaneous values of the traction length of the traction force.

The traction apparatus in accordance with the operation can thus be used, for example, in the implanting of anterior cruciate ligaments for the purpose of tightening the ligament fixed to the femur in order to carry out the fixing of the ligament to the tibia at a ligament tension matching the natural movement of the knee joint.

In order to determine the ligament tension and/or the ligament length on the implanting of anterior cruciate ligaments, an upper working section can be provided with a support and/or fastening section via which the apparatus can be supported at and/or fastened to the tibia.

The working sections can each be provided with at least one cut-out for the passage of a fixing tool and of a fixing member to fix the ligament in the tibia. The tool is, for example, a screwdriver with which a displacement screw forming the fixing member can be screwed into a bore formed in the tibia to fix the ligament to be implanted and inserted into the bore. The cut-out formed in the working sections is preferably dimensioned such that the screwdriver can be introduced along the ligament with a mounted displacement screw.

It is furthermore proposed that the upper working section is provided with at least one cut-out for the passage of the ligament and/or of a drawing member connected to the ligament.

Furthermore, a lower working section can be provided with at least one fastening section for the fastening of the ligament or of a drawing member connected to the ligament.

Provision is made in accordance with a further preferred embodiment of the invention for the support mount for the cylinder to be made at least partly tubular and for the cylinder to be insertable into the support mount along the tube axis, with the support mount having an insertion opening, in particular a slot-shaped insertion opening, for the lateral insertion of a fluid line connected to the cylinder.

It is hereby possible in an advantageous manner on the preparation of the traction apparatus for the cylinder—if it is intended to be introduced into the support mount with that end at the front at which it is connected to the fluid line—already to be able to be connected to the fluid line such that it is not necessary at any time during the assembly of the traction apparatus to separate the fluid connection between the fluid line and the cylinder.

It is furthermore proposed in accordance with a preferred embodiment for a carrier to be provide for a cutting template, in particular in the form of a cutting block, which can be coupled to a carrier member to which the support mount for the cylinder and the working section which can be coupled to the cylinder are connected.

A cutting block for the preparation of the femur or of the femur condyles can be brought into any desired adjustable height relative to the carrier member and thus to the working sections of the traction apparatus by means of such a carrier.

The carrier preferably includes a platform serving as a support for the cutting gauge and a carrier bar which can be coupled to the carrier member, with the carrier bar carrying the platform at is one end and being insertable into an adjustment passage of the support body in which the carrier bar is adjustable relative to the carrier member and is fixable in a plurality of positions, in particular of discretely distributed positions, on the support body.

Provision is preferably made for the support bar and the inner wall of the adjustment passage to be provided with structures, in particular rib-shaped structures, which cooperate to fix its relative position.

The adjustment arrangement of carrier bar and adjustment passage is preferably made in a self-locking manner.

The support bar can be made in fork-shape at least regionally and can include fork arms which can be pressed together against a restoring force and which are in particular provided with structures on their outer side facing away from one another. The carrier bar can hereby be released from the carrier member and moved in the adjustment passage simply by pressing the two fork arms together in order to be brought into a new position relative to the carrier member.

The fork arms of the carrier bar can in particular be provided with structures in the form of differently oriented rib structures at their sides pointing in opposite directions.

Provision is made in a further preferred embodiment for the carrier bar and the carrier member to cooperate in the manner of a ratchet at least on adjustment movements along the traction axis. The carrier bar thus only needs to be moved along the adjustment passage in one direction, e.g. to raise the platform, without pressing the fork arms together.

In accordance with a further embodiment, the carrier bar can furthermore be pivoted from a parallel alignment to the traction axis with respect to the carrier member, in particular in a plane fixed by two piston-in-cylinder arrangements arranged at both sides of the adjustment passage. The platform, and thus a cutting block lying on the platform, can hereby be set obliquely with respect to the traction axis.

The carrier bar can have a pivot head which is matched to the adjustment passage and about which the carrier bar is pivotable.

Furthermore, the adjustment passage can expand in the direction extending away from the platform when the carrier bar is inserted.

The carrier bar can be provided with a display device, in particular in the form of a scale, which is visible from the outside via a reading window formed in a wall of the carrier member in the state inserted into the adjustment passage. The upper working section can furthermore be provided with a display device, in particular in the form of a scale. In this manner, the working level of the platform and of the upper working section can be read off with respect to the carrier member, from which the vertical position of the platform, and thus of a cutting block lying on the platform, can be determined with respect to the upper working section.

Provision is furthermore made in accordance with the invention for the platform to be disposed at least substantially outside the projection of the tibia along the traction axis when the working sections are introduced between the femur and the tibia to spread the knee apart. Furthermore, the platform can be disposed in front of a functional block which extends parallel to the traction axis and to which the working section couplable to the cylinder is firmly connected.

A particularly simple and problem-free handling of the traction apparatus can be realized by such an arrangement of the platform.

Figure 5:
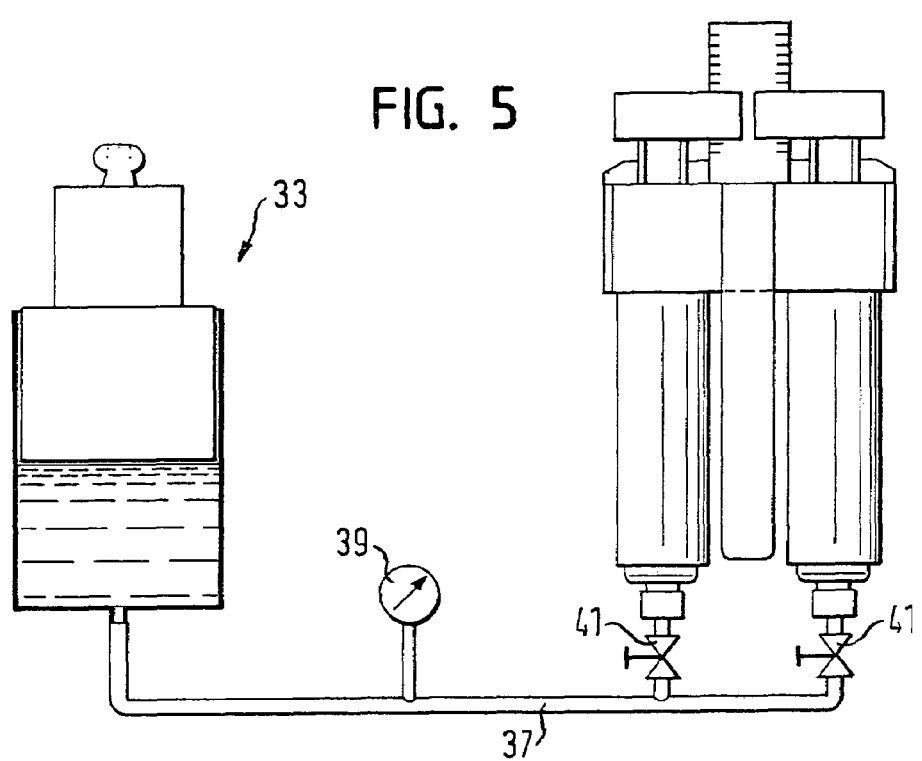
Figure 6:
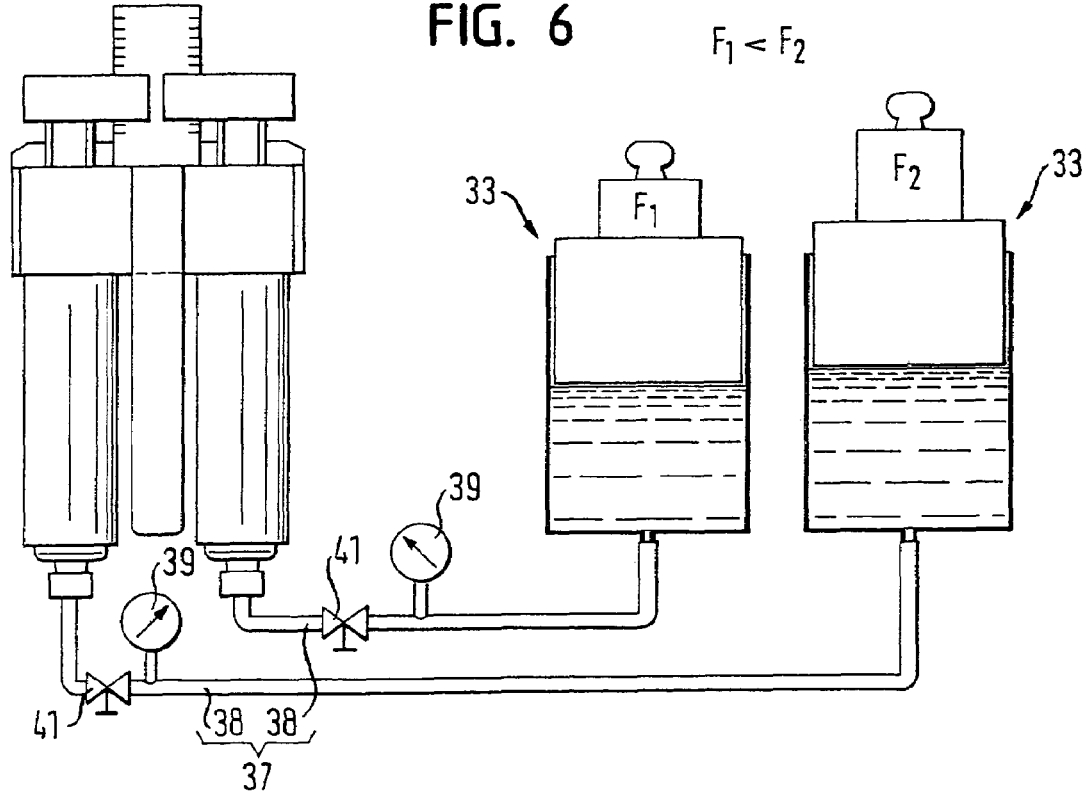
Figure 7:
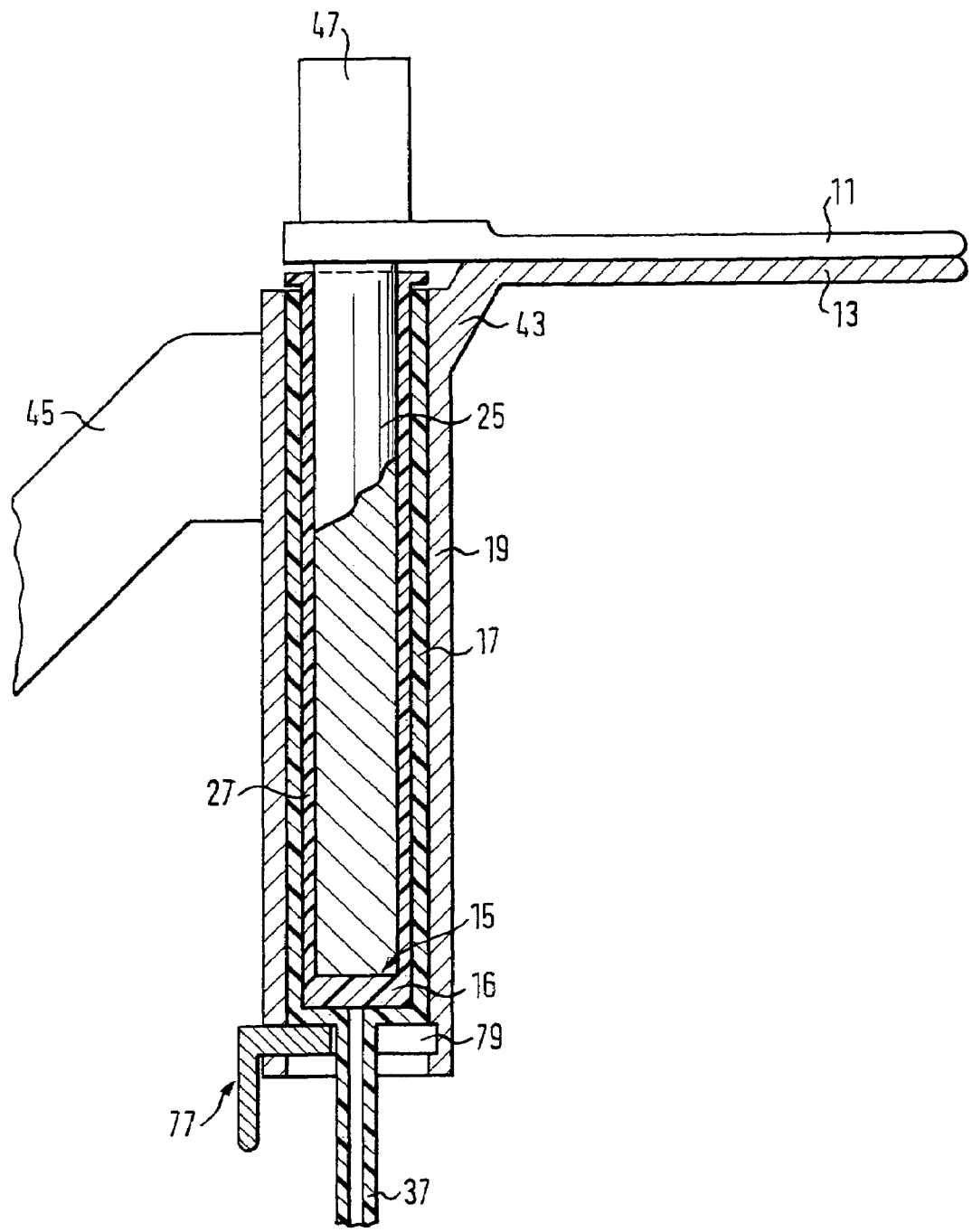
Figure 8:
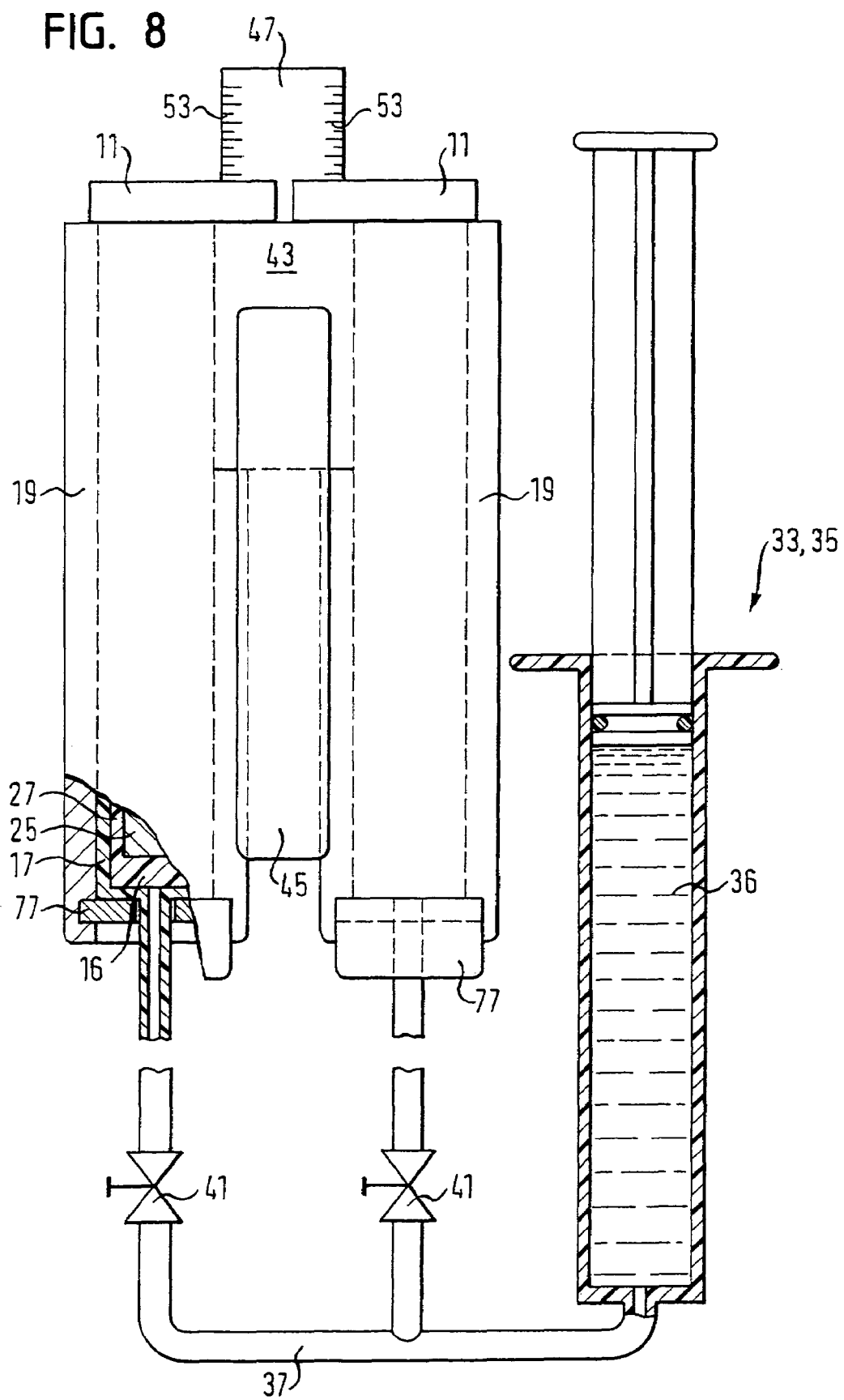
Figure 9:
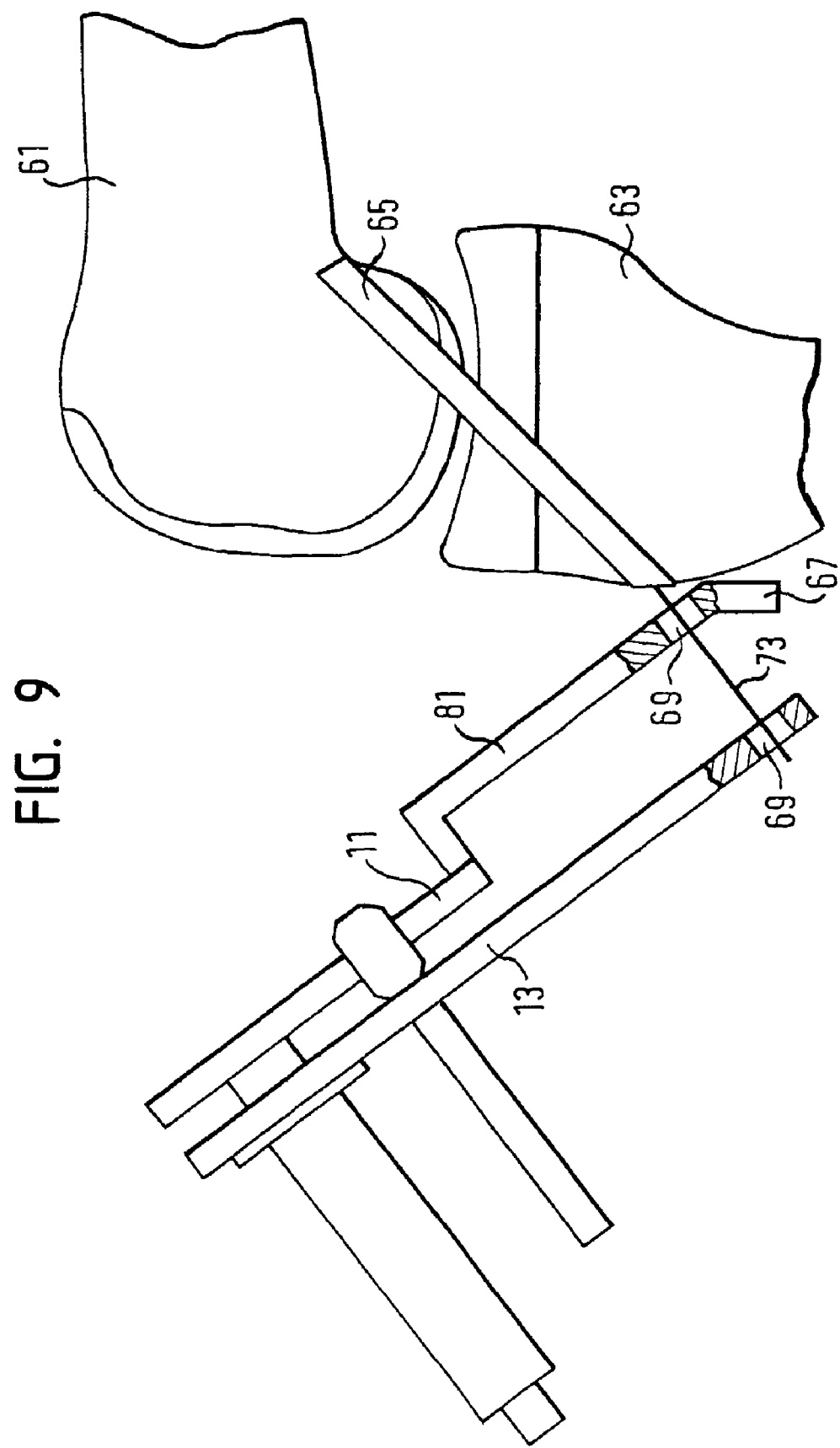
Figure 10:
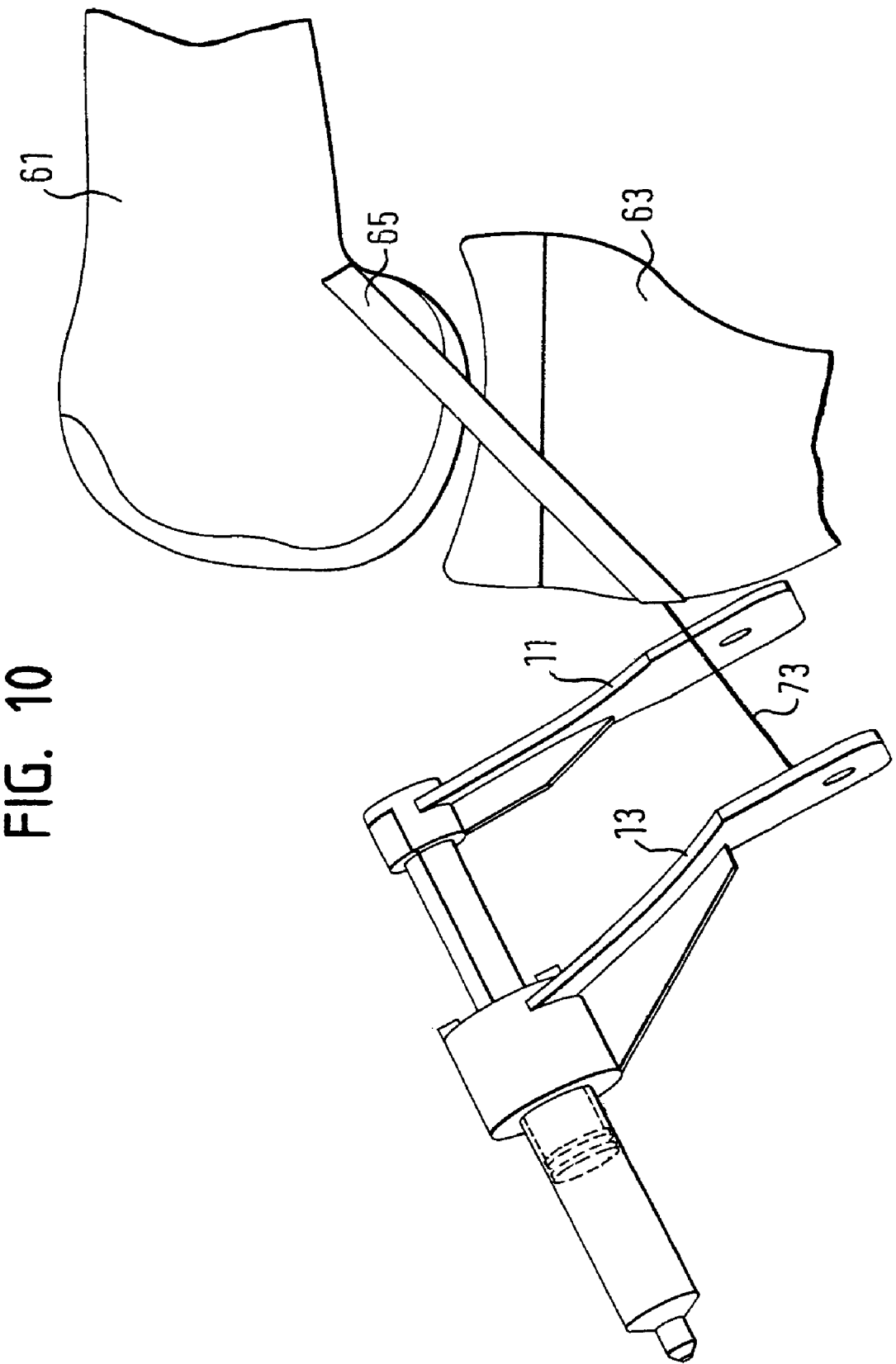
Figure 11:
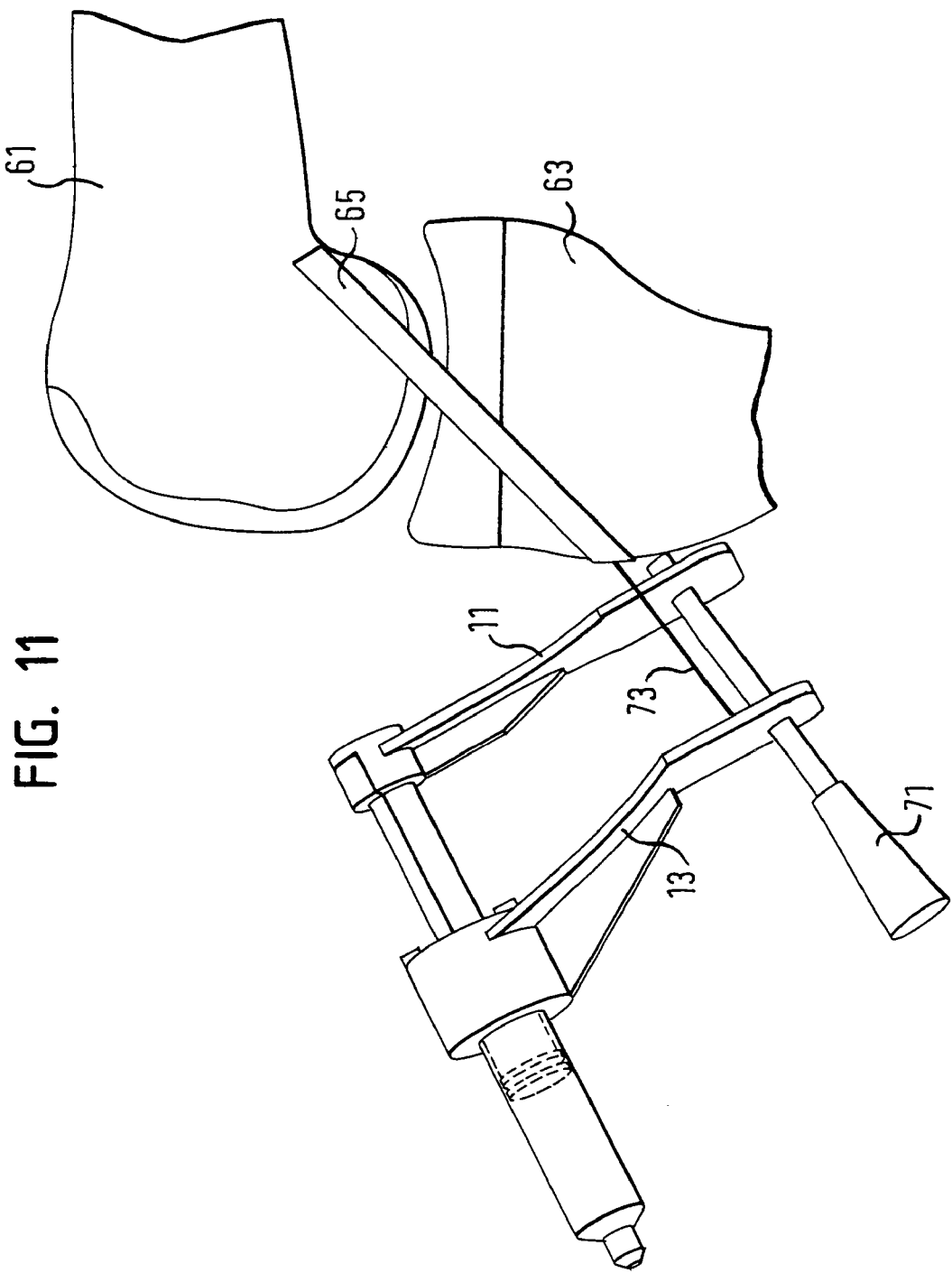
Figure 12:
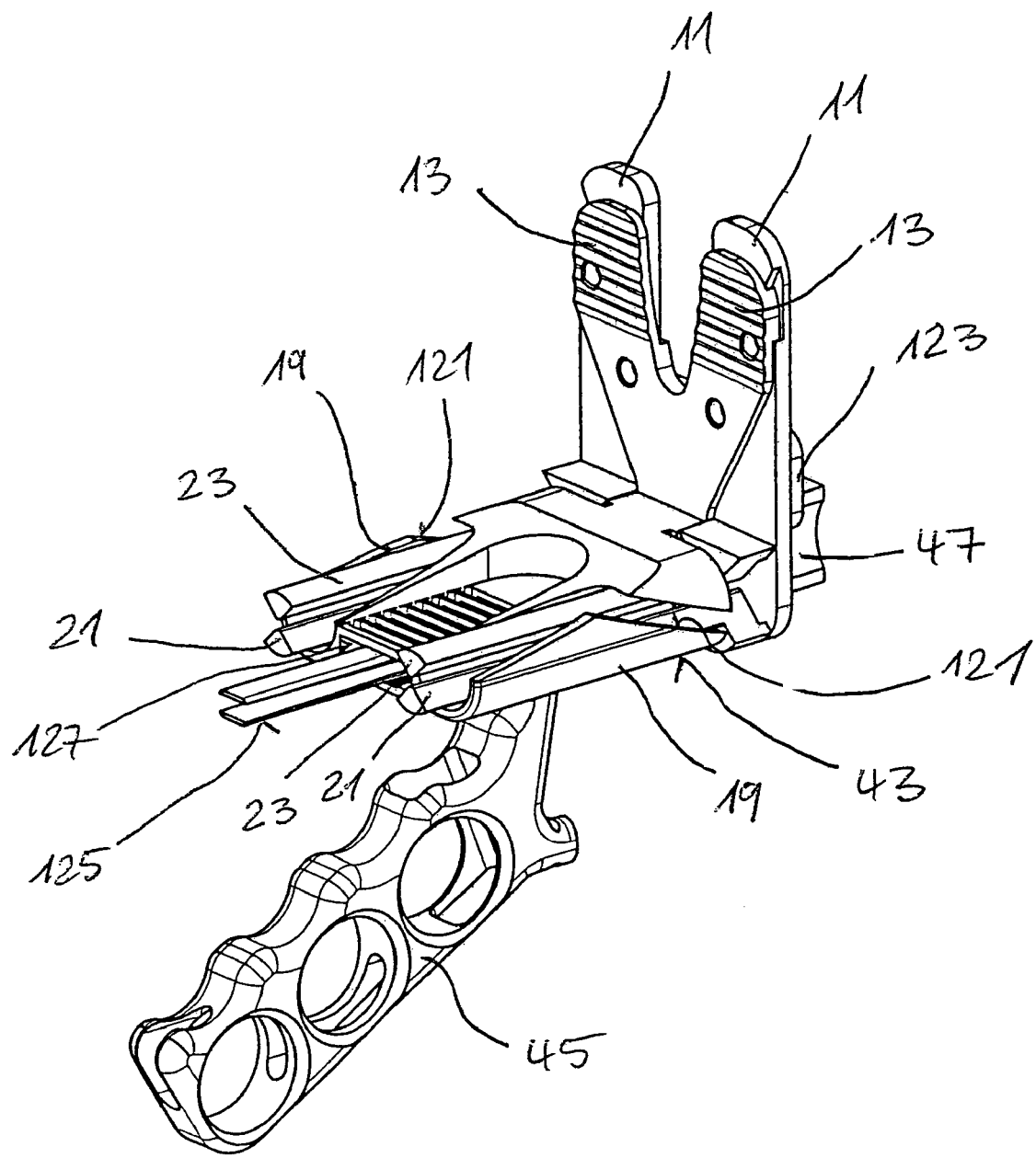
Figure 20:
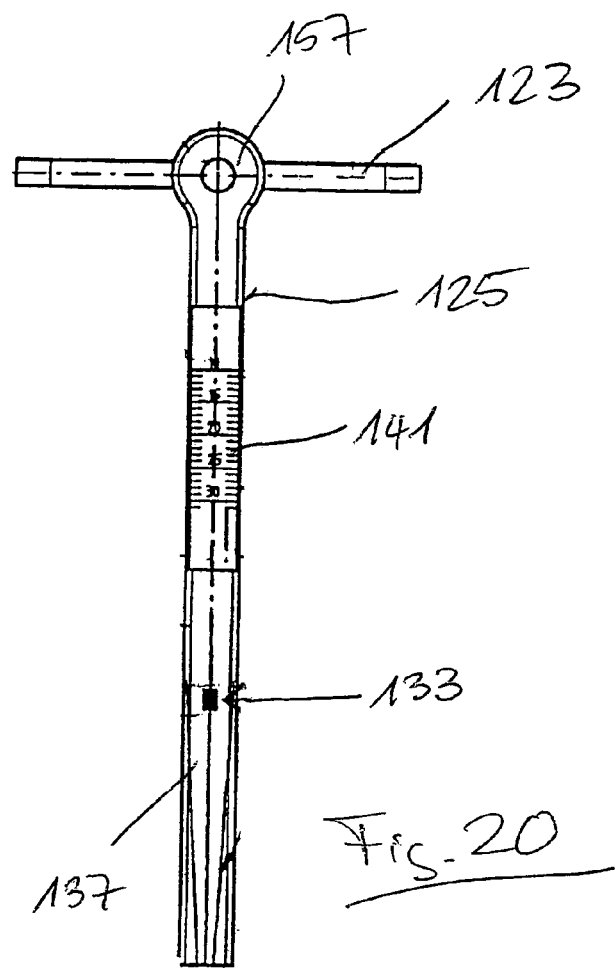
Figure 21:
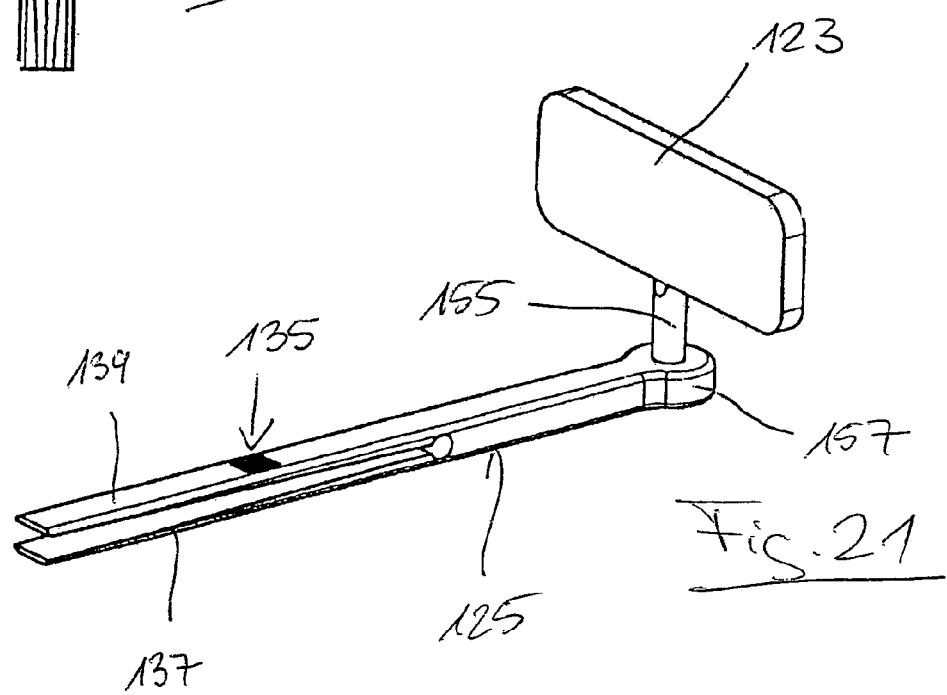

The invention will be described in the following by way of example with reference to the drawing. There are shown:

FIG. 1 a longitudinal section through a traction apparatus in accordance with an embodiment of the invention;

FIG. 2 a front view of the traction apparatus of FIG. 1;

FIG. 2A is a view similar to FIG. 2 of another traction apparatus of the present invention that includes a functional block having an inclined abutment surface;

FIG. 3 a plan view of the traction apparatus of FIG. 1 without cylinders and without upper working sections;

FIG. 4 a plan view in accordance with FIG. 3 with inserted cylinders and upper working sections;

FIG. 5 a possibility for the connection of a traction apparatus in accordance with the invention to a fluid supply device;

FIG. 6 a possibility for the connection of a traction apparatus in accordance with the invention to two fluid supply devices operable independently of one another;

FIG. 7 a part longitudinal section through a traction apparatus in accordance with a further embodiment of the invention;

FIG. 8 the traction apparatus of FIG. 7 as a component of a closed hydraulic system;

FIGS. 9-11 the use of traction apparatuses in accordance with the invention on the implanting of an anterior cruciate ligament;

FIG. 12 a perspective view of a traction apparatus in accordance with a further embodiment of the invention;

FIGS. 13-15 different views of the traction apparatus of FIG. 12;

FIGS. 16-19 different views of a carrier member of the traction apparatus of FIG. 12;

FIGS. 20 and 21 different views of a carrier of the traction apparatus of FIG. 12;

FIG. 22 different views of a carrier bar of the carrier of FIGS. 20 and 21; and

FIGS. 23 and 24 a respective perspective view of a left hand or right hand upper working section with associated reinforcement inserts.

The embodiment shown in FIGS. 1-4 of a hydraulic traction apparatus in accordance with the invention includes a carrier member 43 which bears a handle 45 at one side and is connected at the opposite side in one part to a tongue-shaped platform 13 which forms a lower working section of the traction apparatus.

Furthermore, two passages extending in parallel are formed in the carrier member 43 and each merge downwardly into a support tube 19 fastened to the carrier member 43. The carrier member 43 has a functional block 47 at the side remote from the support tubes 19 which is arranged centrally between the passages and which will be looked at more detail below.

A respective cylinder 17 of a piston in cylinder arrangement provided in this embodiment in the form of a commercial disposable syringe is inserted into the passages of the carrier member 43. In their desired positions, the cylinders 17 are supported in each case with tabs 59 at a correspondingly formed ring shoulder 44 of the carrier member 43. The outer walls of the cylinders 17 each contact the inner wall of the support tube 19. Fluid lines, not shown in FIGS. 1-4, can be screwed onto connection sections 55 each formed at the free ends of the cylinders 17.

Each disposable syringe furthermore includes a piston 15 having a piston section 16 contacting the inner wall of the cylinder 17 in a fluid impermeable manner and having a piston rod 27 which merges at its free end remote from the piston section 16 into a head section 57, also known as a mushroom, broadened radially with respect to the piston rod 27.

The guiding of the piston 15 in the region of the piston rod 27 takes place by a cross-shaped rib structure 31 (cf. the cross-sectional view A-A at the bottom of FIG. 1). The piston rod 27 includes four ribs, with two adjacent ribs in each case forming an angle of 90°. With the piston 15 inserted into the cylinder 17, the ribs of the piston rod 27 bound chambers 29 within the cylinder 17. In the embodiment shown, two mutually oppositely disposed chambers (cf. the cross-sectional view A-A) are each completely filled by a reinforcement insert 21 or 23 respectively.

The one reinforcement insert 21 is connected in one piece to a further tongue-shaped platform 11 which forms the upper working section of the traction apparatus in accordance with the invention. The other reinforcement insert 23 is provided in the form of a separate component. The insert 21 connected to the upper platform 11, the separate insert 23 as well as the piston 15 are first assembled to form a piston unit before it is inserted as a whole into the cylinder 17, with the cylinder 17 previously already being able to have been inserted into the corresponding passage of the carrier member 43.

On the assembly of the piston unit, the mushroom-shaped head 57 of the piston rod 27 is first inserted with one side into a slot-like reception between the upper platform 11 and a flange section 24 which extends parallel to the upper platform 11 and which is a component of a transition section 49 between the upper platform 11 and the reinforcement insert 21 connected to it.

The separate reinforcement insert 23 is provided with a corresponding flange section 24 so that the head 57 of the piston rod 27 is spatially fixed between the two inserts 21, 23 and the upper platform 11.

On the insertion of the head 57 into the reception slot formed in the transition section 49, the insert 21 connected to the upper platform 11 moves into the corresponding chamber (cf. cross-sectional view A-A in FIG. 1) of the rib structure 31. The same applies correspondingly on the insertion of the separate insert 23.

Consequently two chambers disposed opposite one another within the cylinder 17 are completely filled with material for each position of the piston 15 with the two inserts 21, 23, whereby the piston unit is given a high bending strength. The cylinder 17 is furthermore supported from the outside by the support tube 19 such that overall a piston in cylinder arrangement with bending strength is created which always ensures sufficient parallelism between the two platforms 11, 13 even with large external forces acting on the two platforms 11, 13. The upper free end of the separate insert 23 advantageously serves as a support for the upper platform 11 in the region of the flange section 24.

The front view of FIG. 2 in particular shows the handle 45 which is arranged centrally with respect to the support tubes 19 from which the cylinders 17 each project a little at the bottom. Furthermore, the sides of the inserts 21 fixedly connected to the upper platform 11 and facing in the direction of the handle 45 as well as in each case the sides of the two ribs of the rib structure 31 bounding the two chambers for the insert 21 can be recognized in FIG. 2.

The functional block 47 is provided at its side facing in the direction of the handle 45 with scales 53 at which the respective piston position can be read off, whereby a measure for the traction length is available.

As can in particular be seen from FIG. 4, the functional block 47 is engaged around by the transition sections 49 in a corner region in each case and thus serves as a guide for the assemblies consisting in each case of the piston unit and of the upper platform 11. In this respect, the transition sections 49 each represent a guide section for the relevant assemblies which reliably prevents a relative rotation of the assembly relative to the carrier member 43 about the longitudinal axis of the piston in cylinder unit and thus ensures a constant orientation of the respective upper platform 11.

As illustrated in FIG. 2A, the functional block 47 can be made trapezoidal in shape such that it broadens upwardly so that—unlike in FIG. 2—the outer sides 53 do not extend in parallel, but inclined with respect to the traction direction. A slight clearance between the guide section 49 and the functional block 47, which is still present with a completely inserted piston unit, is reduced in this manner as the traction length increases.

FIG. 3, in which the traction apparatus in accordance with the invention is shown without piston units inserted into the cylinders 17 and thus without upper platforms 11, in particular shows the tabs 59 which project at right angles with respect to the longitudinal axis and with which the cylinders 17 each lie on the ring shoulders 44 of the carrier member 43 provided for this.

As FIG. 5 shows, both piston in cylinder arrangements can be connected to a common fluid supply device 33 only shown in principle here. On/off valves 41 make it possible to operate the two units independently of one another to the extent that the one unit is fixed by closing the relevant valve 41 at the traction length just reached and the traction is continued in the other unit by leaving the valve 41 open. Work can hereby be carried out, for example, with an asymmetrical distribution of forces when spreading a knee.

A measure for the traction force acting between the working sections can be read off at a pressure display device 39 connected to the common fluid line 37.

FIG. 6 shows an example in which the two piston in cylinder arrangements of the traction apparatus can be operated completely independently of one another. A separate fluid supply unit 33, which is connected to the respective cylinder via an individual line 38, is associated with each unit. An on/off valve 41 for the alternative blocking or releasing of the individual line 38 as well as a pressure display device 39 are associated with each individual line 38.

The fluid supply devices 33 shown in FIGS. 5 and 6 can be commercial disposable syringes 33. They can be of the same design as the disposable syringes forming the piston in cylinder arrangements 15, 17 provided that the fluid volume required overall for the two piston in cylinder arrangements 15, 17 can be made available with a single disposable syringe. This is the case at least for the greater part of operations carried out with the aid of the traction apparatus in accordance with the invention, since in most cases the aim is anyway to avoid an excessive moving out of the piston units.

In the further embodiment of a traction apparatus in accordance with the invention in accordance with FIGS. 7 and 8, only one single reinforcement insert 25 is provided which is made fixedly, and in particular in one part, with the upper platform 11. The insert 25 is a full cylinder whose outer wall contacts the inner wall of a piston rod 27, which is tubular in this embodiment, such that the interior of the piston rod 27 is completely filled by the insert 25.

The cylinder 17 of the piston in cylinder arrangement which is connected in one piece to a fluid line 37 only shown in part in FIG. 7 is inserted into the support tube 19 connected to the carrier member 43 from below in this embodiment. A latching device 77 with a fork-like latching section 79 serves for the securing of the inserted cylinder 17. For reasons explained in the following, the insertion of the cylinder 17 into the support tube 19 takes place with the piston 15 inserted into the cylinder 17 such that subsequently, for the completion of the traction apparatus, only the fully cylindrical inserts 25 have to be inserted into the tubular piston rods 27.

As FIG. 8 shows, the two piston in cylinder arrangements are components of a closed hydraulic system which moreover includes a common fluid supply device 33 in the form of a disposable syringe 35, a hydraulic fluid 36, in particular water, as well as a fluid line 37 connecting the two cylinders with the syringe 33 and having on/off valves 41 each in the form of a stopcock. In addition, the fluid line 37 can be provided with one or more pressure display apparatuses. This hydraulic systems is produced as a fully assembled unit, in particular already filled with the hydraulic fluid 36, and is delivered sterilized as a whole.

The handling of the traction apparatus in accordance with the invention is hereby extremely simple for the operator. Optionally, subsequent to a sterilization of the non-hydraulic systems, that is of the remaining components of the traction apparatus not belonging to the aforesaid hydraulic system, only the two piston in cylinder arrangements of the sterile hydraulic system have to be inserted into the support tubes 19 from below and be secured by means of the latching devices 77 ad the reinforcement inserts 25 have to be inserted from above with the upper tongues 11.

In deviation from the two embodiments described above, the traction apparatus in accordance with the invention can also only include a single piston in cylinder arrangement 15, 17 with a single pair of tongue-shaped platforms 11, 13.

The components of the piston in cylinder arrangements are preferably plastic parts manufactured by the injection molding process, whereas at least the support tubes 19 and the reinforcement inserts 21, 23, 25 are produced from a material of higher bending strength, for example from metal or from a fiber reinforced plastic, which can, for example, be steam sterilized due to their reuse in a hospital.

The tractions apparatuses described in FIGS. 1 to 8 serve for the spreading of the knee, as has been described in the introductory part, and make the so-called "oscillating" of the knee joint possible for the determination of the optimum spacing between the femur and the tibia determined by the natural tension of the ligaments while simultaneously displaying measured values characteristic for the relevant knee for the instantaneous parameters of traction length and traction force.

FIGS. 9 to 11 show the use of traction apparatuses in accordance with the invention on the implanting of an anterior cruciate ligament. In such an operation, the ligament 65 is inserted into a bore previously formed in the femur 61 and is fixed there by means of a displacement screw (not shown) screwed in along the jacket line of the ligament 65. The ligament is subsequently pulled forwardly through a bore previously formed in the tibia 63 in order to be fixed in this tibia bore by means of a further displacement screw (not shown).

The further use of the traction apparatus in accordance with the invention comes into play here:

Whereas it was previously customary to give the ligament 65 a pre-determined bias with the aid of a spring balance prior to the tightening of the tibia displacement screw to fix the ligament 65 under this bias, with the spring balance being pulled outwardly without any further support, the spring balance is now replaced by the traction apparatus in accordance with the invention which can have either a single piston in cylinder arrangement or—as in the embodiments described above in connection with FIGS. 1-8— two piston in cylinder arrangements arranged in parallel and thus upper platforms 11.

In the following, for reasons of simplicity, a "mono variant" is assumed with only one single piston in cylinder arrangement such as is shown, for example in FIGS. 10 and 11.

During surgery, the traction apparatus is supported at the tibia 63 at its upper working platform 11, which—as shown in FIG. 9—can be provided for this purpose with a special mount 81 whose front free end is formed by a support section and/or fastening section which is angled or which can be angled. The ligament 65 and, optionally,—as shown in FIGS. 9-11— a drawing member 73, for example in the form of a wire, connected to the ligament 65 is pulled through cut-outs 69 formed in both platforms 11, 13 and fastened to the lower platform 3. The cut-outs 69 are dimensioned such that a screwdriver 71 shown schematically in FIG. 11 can be inserted along the ligament 65 with a positioned displacement screw to fix the ligament 65 having the correct bias in the tibia 63.

It is advantageously possibly by means of the traction apparatus in accordance with the invention to measure the ligament tension or to determine a measure for the ligament tension prior to the final fixing of the ligament 65 in the tibia 63 either at all possible positions or at some selected positions, i.e. angles of deflection, of the knee to optionally set a ligament tension by varying the ligament length which is suitable for all possible angles of deflection and thus for the normal motion of the knee joint. The measure for the ligament tension is determined using a pressure display device such as has been described, for example, in connection with the embodiments of FIGS. 1-8, whereas the measure for the ligament length is given by the traction length which can be read off at a display device, e.g. in the form of a scale, such as has likewise been described, for example in connection with the embodiments of FIGS. 1-8.

During the determination of the optimum length of the ligament 65 to be implanted, the upper platform 11 can, for example, be fastened to the tibia 63 with the aid of fracture nails to provide defined geometrical relationships.

The further embodiment of a traction apparatus in accordance with the invention described with reference to FIGS. 12 to 24 corresponds to the piston-in-cylinder arrangements not shown here with respect to the principle of the reinforcement and generally to the first embodiment described with reference to FIGS. 1 to 4 with respect to further aspects which result from the following description.

The two upper working sections or tongues 11 (cf. in particular FIGS. 12-15 and 23 and 24) are firmly connected to a rear reinforcement insert 21 in the region of their rear end. Separate reinforcement inserts 23 serve for the completion of the piston reinforcement in accordance with the first embodiment (FIG. 1). As already mentioned, the piston and the cylinder of the piston-in-cylinder arrangements, which are in turn respectively formed by a commercial disposable syringe, are not shown. However, the free space 153 for the piston, including the region for the head section or mushroom of the piston can in particular be recognized between the flange sections 24 of the reinforcement inserts 21, 23 in FIG. 13.

In the assembled state of the traction apparatus, the piston, including the reinforcement inserts 21, 32, is inserted into the cylinder of the respective piston-in-cylinder arrangement and the cylinder is in turn introduced into a respective support mount 19 which is formed on a central carrier member 43 which will be described in more detail in the following. The support mounts 19 are each made partly tubular and are provided in the form of a support tube cut open obliquely from below (FIG. 19). The cut-away region points forwardly in this process, i.e. in the direction of the free ends of the working tongues 11,13, so that a support is provided over the whole length of the support mounts 19 in the opposite direction, i.e. rearwardly. The support mounts 19 are respectively provided with a slot-like insertion opening 121 which extends from the upper insertion opening up to and into the upper region of the lower opening of the support mount 19 extending obliquely due to the cutting open.

The lateral insertion openings 121 advantageously allow the cylinder to be inserted into the respective support mount 19 from above with a fluid line connected from below when assembling the traction apparatus in that the fluid line is simply inserted from the side via the insertion opening 121. The fluid line can thus always remain firmly connected to the cylinder, with it, however, not being necessary—as is, for instance, the case with the embodiment of FIG. 7—to introduce the cylinder from below and to provide a latching device.

The lower working plate, which has an approximately Y-shaped outline and whose limbs are formed by the two lower working tongues 13, is secured via its rear end in a slot 149 formed on the carrier member 43 (FIG. 19).

The carrier member 43 furthermore has a throughgoing adjustment passage 127 which extends parallel to the traction axis and which extends between the two support mounts 19. The adjustment passage 127 serves for the mounting of a carrier bar 125 of a carrier which moreover has a platform 123 and which will be described in more detail in the following in connection with FIGS. 20 to 22.

A reading window 143 to the adjustment passage 127 is formed in the rear wall of the carrier member 43 and via this the rear side of the carrier bar 125 introduced into the adjustment passage 127 is visible and a scale 141 attached to this rear side (FIG. 20) is readable. A handle 45 of the traction apparatus is connected to the rear wall of the carrier member 43 beneath the reading window 143.

The adjustment passage 127 and the carrier bar 125 are provided with structures 129, 131, 133, 135 in the form of rib structures which will be looked at in more detail in the following.

In accordance with the embodiment of FIGS. 1 to 4, a functional block 47 is provided which extends along the traction axis. The functional block 147 is an integral component of the central carrier member 43.

The functional block 47 serves inter alia for the guiding of the upper working tongues 11. Furthermore, a pivot head 157 of the carrier bar 125 and a connection piece 155 (FIG. 15), via which the platform 123 is connected to the carrier bar 125 and which extends perpendicular to the carrier bar 125, are mounted in the functional block 47 (FIG. 15).

The platform 123 is arranged directly in front of the functional block 47. The width of the platform 123 is slightly lower than the total width of the upper working section 11, whereas the depth of the platform 123 is dimensioned such that—considered from the functional block 47—the platform ends before the lower working section divides into the two working tongues 13.

The platform 123 is hereby located outside the projection of the tibia along the traction axis with working sections 11, 13 introduced between the femur and the tibia for the spreading apart of the knee.

In particular the arrangement and the design of the structures 129, 131 which are formed on the inner sides of the adjustment passage 127 and which cooperate with the carrier bar 125 can be seen from FIGS. 16 to 19.

A structure 129 in the form of ribs or webs which extend transversely to the traction axis and which are formed in the lower region of the adjustment passage 127 serves for the fixing of the carrier bar 122 at different vertical positions. As in particular FIG. 18 shows, the adjustment passage 127 is expanded downwardly, starting from the vertical level of the upper insertion openings of the support mounts 19, such that the width of the adjustment passage 127 increases constantly. The transverse structure 129 is formed in the lower region of this widening of the adjustment passage 127 which has the shape of a slim trapezoid in cross-section.

The adjustment passage 127 is provided with an elongate structure 131 in the form of ribs extending parallel to the traction axis (FIG. 17) on the opposite inner wall (FIG. 18, left hand representation). This structure 131 serves to fix the carrier bar 125 at different oblique positions, which will be looked at in more detail in the following.

FIGS. 20 to 22 show that the carrier bar 125 is regionally designed as a fork with two fork arms 137, 139. The spacing of the fork arms 137, 139 from one another is matched to the spacing of the inner sides of the adjustment passage 127 of the carrier member 43 provided with the structures 129, 131 such that structures 133, 135 formed at the outer sides of the fork arms 137, 139 facing away from one another are in engagement with the structures 131, 129 of the adjustment passage 127 when the carrier bar 125 is introduced into the adjustment passage 127.

The engagement between the structures can be released and the carrier bar 125 can be moved relative to the carrier member 43 in the adjustment passage 127 by pressing the two fork arms 137, 139 together against their restoring force.

It can in particular be seen from FIG. 22 that the structure 133 of the carrier bar 125 is provided in the form of longitudinal ribs, whereas the structure 135 formed on the opposite side includes transverse ribs which—as the detail A at the top right in FIG. 22 shows—have the shape of saw teeth such that movements of the carrier bar 125 out of the adjustment passage 127 are possible without pressing the fork arms 137, 139 together, but movements of the support bar 125 downwardly into the adjustment passage 127 are blocked and are only possible with fork arms 137, 139 pressed together. In this respect, the carrier bar 125 and the adjustment passage 127 cooperate in the manner of a ratchet with respect to movements parallel to the traction axis due to their structures 135, 129.

The diameter of the upper pivot head 157 of the carrier bar 125 which has a partly circular outer shape and to which the platform 123 is connected via the connection piece 155 corresponds to the constant width of the adjustment passage 127 above the widening.

The carrier bar 125 can consequently be pivoted about the pivot head 157 guided in the adjustment passage 127 in the plane fixed by the middle axes of the two partially tubular support mounts 19, with the pivot axis extending through the connection piece 155 which connects the platform 123 to the pivot head 157 and can rotate in a cut-out 159 of the functional block 47 (FIGS. 16, 18, 19). Movements of the pivot head 157 received in the functional block 47 are not possible transverse to the traction axis.

When the fork arms 137, 139 are pressed together and the structures 129, 135 or 131, 133 respectively are thus out of engagement, the carrier bar 125 in the adjustment passage 127 can so-to-say swing like a pendulum about its pivot head 157, with the movement clearance required for this being provided for the carrier bar 125 by the downward widening of the adjustment passage 127.

The pivoting of the carrier bar 125 in the adjustment passage 127 has the consequence of a tilting of the platform 123 out of the neutral position perpendicular to the traction axis. The elongate structures 131, 133 permit a fixing of the carrier bar 125 in the state deflected out of a parallel alignment with respect to the traction axis, i.e. an oblique position of the platform 123 can be fixed by means of the structures 131, 133. The structures 133, 135, in particular the transverse structure 135, formed on the carrier bar 125 are so deep and are dimensioned in their widths and lengths respectively such that the carrier bar 125 latches into place despite the oblique position.

The carrier member 43 is provided at its lower region with a display device in the form of a scale which is not shown and at which a measure can be read off for a respective pivot position of the carrier bar 125 and thus for the respective oblique position of the platform 123.

In FIG. 20, the already mentioned scale 141 is shown which is formed at the outer side of the rear fork arm 137 and which is visible to the surgeon from the outside via the reading window 143 formed in the rear wall of the carrier member 43 (FIG. 14). The vertical position of the carrier bar 125 and thus of the platform 123 with respect to the carrier member 43 can be determined via this scale 141.

FIGS. 23 and 24 show the upper working tongues 11 and the reinforcement inserts 21, 23. Inwardly projecting tabs 147, whose rear sides extend perpendicular to the platform formed by the tongues 11, are furthermore shown. As FIG. 14 shows, the rear side of the tab 147 (FIG. 24) connected to the right hand working tongue and visible to the surgeon during the operation is provided with the already mentioned scale 145 via which the vertical position of the upper working platform 11 with respect to the carrier member 43 can be read off.

Furthermore, cut-outs 151 formed at the lower sides of the upper tongues 11 are shown in FIGS. 23 and 24 into which elevations formed at the upper side of the lower working platform 13 engage when the two working platforms 11, 13 are completely moved together (FIGS. 12 and 13).

It is furthermore possible to attach further apparatuses to the platform 123 such as a pivot apparatus which is pivotable about a medullary nail inserted in the femur and which permits a balancing of the ligament tension under a pre-set pretension which can be read off at the hydraulics of the piston-in-cylinder arrangements formed by the disposable syringes.

REFERENCE NUMERAL LIST 11 upper working section, upper tongue
13 lower working section, lower tongue
15 piston
16 piston section
17 cylinder
19 support mount, support tube
21 reinforcement insert
23 reinforcement insert
24 flange section
25 reinforcement insert
27 piston rod
29 chamber
31 rib structure
33 fluid supply device
35 syringe
36 hydraulic fluid
37 fluid line
39 pressure display device
41 on/off valve
43 carrier member
44 ring shoulder
45 handle
47 functional block
49 guide section
51 abutment surface
53 display device, scale
55 connection section
57 head section, mushroom
59 tab
61 femur
63 tibia
65 cruciate ligament
67 support section and/or fastening section
69 cut-out
71 fixing tool, screwdriver
73 drawing member
77 latching device
79 fork-like latching section
81 mount
121 insertion opening
123 platform
125 carrier bar
127 adjustment passage
129 structure
131 structure
133 structure
135 structure
137 fork arm
139 form ark
141 display device, scale
143 reading window
145 display device, scale
147 tab
149 slot
151 cut-out
153 free space for piston
155 connection piece
157 pivot head
159 cut-out for connection piece

The invention claimed is:

1. A hydraulic traction apparatus for surgery, in particular for knee surgery, comprising:
   at least a first working section and a second working section, the first working section being movable relative to the second working section;
   at least one exchangeable piston in cylinder arrangement made of plastic whose piston is releasably coupled to the first working section for movement therewith, said piston comprising a piston section positioned to communicate with hydraulic fluid and a piston shaft, and whose cylinder is releasably coupled to the second working section, the first working section being movable relative to the cylinder;
   an outer support mount supporting the cylinder from the outside; and
   at least one inner reinforcement insert which can be inserted into the cylinder together with the piston to at least partially surround the piston shaft, the at least one inner reinforcement insert coupled to the piston for movement therewith relative to the cylinder.

2. A traction apparatus in accordance with claim 1, wherein the piston and the cylinder are each disposable articles produced by the injection molding method.

3. A traction apparatus in accordance with claim 1, wherein the piston and the reinforcement insert form a compact piston unit in the assembled state which completely fills the interior of the cylinder at least over a partial peripheral region.

4. A traction apparatus in accordance with claim 1, wherein the piston in cylinder arrangement is formed by a commercial disposable syringe.

5. A traction apparatus in accordance with claim 1, comprising a free space between the inner wall of the cylinder and the piston shaft, said free space at least partly filled by the reinforcement insert.

6. A traction apparatus in accordance with claim 1, comprising at least one chamber, which is present in the cylinder and which is bounded by a rib structure of the piston shaft, which extends up to the inner wall of the cylinder and is in particular one of cross-shaped and X-shaped in cross-section, said at least one chamber at least partly filled by the reinforcement insert.

7. A traction apparatus in accordance with claim 6, comprising at least one pair of chambers disposed opposite one another, each at least partly filled by a reinforcement insert.

8. A traction apparatus in accordance with claim 1, wherein the piston in cylinder arrangement can be coupled to the first and second working sections in the assembled state.

9. A traction apparatus in accordance with claim 1, comprising at least one reinforcement insert fixedly connected to the first working section.

10. A traction apparatus in accordance with claim 1, wherein at least one reinforcement insert is provided in the form of a separate component.

11. A traction apparatus in accordance with claim 1, wherein the support mount for the cylinder and the working section, which can be coupled to the cylinder, are fixedly connected to a carrier member.

12. A traction apparatus in accordance with claim 1, comprising a handle, which is preferably fixedly connected to a carrier member, positioned at the opposite side of the piston in cylinder arrangement from the first and second working sections.

13. A traction apparatus in accordance with claim 1, wherein the second working section, which can be coupled to the cylinder, is fixedly connected to a functional block which extends parallel to the traction direction and which is formed as a security against relative rotation and/or deflection for the working section which can be coupled to the piston.

14. A traction apparatus in accordance with claim 13, wherein the functional block has an outer cross-section deviating from a circular shape and is engaged over, at least over a partial peripheral region, by a guide section of the first working section in a manner secured against relative rotation.

15. A traction apparatus in accordance with claim 13, wherein the functional block has an abutment surface which is slightly inclined with respect to the traction direction, runs toward the longitudinal axis of the piston in cylinder arrangement in the direction of increasing traction length and cooperates with the first working section in a manner securing against deflection.

16. A traction apparatus in accordance with claim 13, wherein the functional block is provided with a display device, in particular in the form of a scale attached to an outer side, at which a measure for the traction length can be read off.

17. A traction apparatus in accordance with claim 1, wherein one of the support mount and the reinforcement insert are produced from a material with a higher bending strength than the plastic of the piston in cylinder arrangement, in particular from one of a metal and a fiber reinforced plastic.

18. A traction apparatus in accordance with claim 1, comprising at least one pressure display device connected to a fluid line connecting the piston in cylinder arrangement to a fluid supply device.

19. A traction apparatus in accordance with claim 1, wherein the piston in cylinder arrangement is a component of a hydraulic system which can be handled as a unit, which can in particular be sterilized and which additionally includes at least one fluid supply device, a fluid line connecting the piston in cylinder arrangement to the fluid supply device as well as a hydraulic fluid, in particular water, and can be coupled to the first and second working sections as a whole.

20. A traction apparatus in accordance with claim 1, comprising at least two piston in cylinder arrangements active in parallel directions in the state coupled to the first and second working sections.

21. A traction apparatus in accordance with claim 20, wherein the piston in cylinder arrangements are connected to a common fluid supply device during use.

22. A traction apparatus in accordance with claim 1, wherein the first and second working sections form a spreading section which can be introduced between the femur and the tibia and which extends substantially perpendicular to the traction direction for the setting of desired spacings between the femur and the tibia.

23. A traction apparatus in accordance with claim 1, wherein the first and second working sections are each formed as tongue-like platforms which extend at least substantially parallel to one another in the assembled state.

* * * * *